US011781134B2

(12) United States Patent
Klein et al.

(10) Patent No.: US 11,781,134 B2
(45) Date of Patent: *Oct. 10, 2023

(54) TARGETED RNA EDITING

(71) Applicant: ProQR Therapeutics II B.V., Leiden (NL)

(72) Inventors: Bart Klein, Leiden (NL); Gerardus Johannes Platenburg, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 586 days.

This patent is subject to a terminal disclaimer.

(21) Appl. No.: 16/807,577

(22) Filed: Mar. 3, 2020

(65) Prior Publication Data

US 2020/0199586 A1 Jun. 25, 2020

Related U.S. Application Data

(63) Continuation of application No. 15/531,164, filed as application No. PCT/EP2015/080347 on Dec. 17, 2015, now Pat. No. 10,676,737.

(30) Foreign Application Priority Data

| Dec. 17, 2014 | (GB) | ................................. | 1422511 |
| Jul. 16, 2015 | (GB) | ................................. | 1512467 |
| Jul. 17, 2015 | (GB) | ................................. | 1512595 |
| Dec. 14, 2015 | (GB) | ................................. | 1521987 |

(51) Int. Cl.
  *C12N 15/11*   (2006.01)
  *C12N 15/113*  (2010.01)
  *C12N 15/90*   (2006.01)

(52) U.S. Cl.
  CPC ............ *C12N 15/11* (2013.01); *C12N 15/113* (2013.01); *C12N 15/907* (2013.01); *C12N 2310/11* (2013.01); *C12N 2310/16* (2013.01); *C12N 2310/315* (2013.01); *C12N 2310/321* (2013.01); *C12N 2310/3519* (2013.01); *C12N 2310/531* (2013.01); *C12N 2310/533* (2013.01)

(58) Field of Classification Search
  None
  See application file for complete search history.

(56) References Cited

U.S. PATENT DOCUMENTS

| 9,650,627 | B1 | 5/2017 | Rosenthal et al. |
| 10,676,737 | B2 | 6/2020 | Klein et al. |
| 10,941,402 | B2 | 3/2021 | Turunen et al. |
| 10,988,763 | B2 | 4/2021 | Turunen et al. |
| 11,274,300 | B2 * | 3/2022 | Aalto ..................... C12N 15/111 |
| 11,390,865 | B2 | 7/2022 | Fukuda et al. |
| 2014/0228556 | A1 | 8/2014 | Fukuda et al. |
| 2014/0357856 | A1 | 12/2014 | Monia et al. |
| 2017/0355985 | A1 | 12/2017 | Dellinger et al. |
| 2019/0218552 | A1 | 7/2019 | Turunen et al. |
| 2019/0330622 | A1 | 10/2019 | Turunen et al. |
| 2019/0352641 | A1 | 11/2019 | Aalto et al. |
| 2020/0199586 | A1 | 6/2020 | Klein et al. |
| 2021/0079393 | A1 | 3/2021 | Boudet et al. |

FOREIGN PATENT DOCUMENTS

| EP | 3323890 A1 | 5/2018 |
| JP | 2008194035 A | 8/2008 |
| WO | WO-2000/066604 A2 | 11/2000 |
| WO | WO-2004/091515 A2 | 10/2004 |
| WO | WO-2005087949 A1 | 9/2005 |
| WO | WO-2005/094370 A2 | 10/2005 |
| WO | WO-2010/064146 A2 | 6/2010 |
| WO | WO-2010115206 A2 | 10/2010 |
| WO | WO-2011005761 A1 | 1/2011 |
| WO | WO-2011/072082 A2 | 6/2011 |
| WO | WO-2011/119887 A1 | 9/2011 |
| WO | WO-2012006241 A2 | 1/2012 |
| WO | WO-2012/138487 A2 | 10/2012 |
| WO | WO-2013/075035 A1 | 5/2013 |
| WO | WO-2014/011053 A1 | 1/2014 |
| WO | WO-2014/012081 A2 | 1/2014 |
| WO | WO-2014010250 A1 | 1/2014 |
| WO | WO-2014/203518 A1 | 12/2014 |
| WO | WO-2015107425 A2 | 7/2015 |
| WO | WO-2016/062886 A1 | 4/2016 |
| WO | WO-2016/079181 A1 | 5/2016 |
| WO | WO-2016/094845 A2 | 6/2016 |
| WO | WO-2016/096938 A1 | 6/2016 |
| WO | WO-2016/097212 A1 | 6/2016 |

(Continued)

OTHER PUBLICATIONS

Shevchenko et al. FEBS Letters 592: 2860-2873 (Year: 2018).*
Bajas et al. (2017) RNA Biology, 14,(9):1223-1231.
Boots et al. (2017) Neurology, 88(22):2098-2106.
Brown et al. (1994) J. Biol. Chem., 269(43): 26801-26805.
Case et al. (2005) J. Comput. Chem., (16): 1668-1688.
Chen et al. (2019) "RNA-Guided Adenosine Deaminases: Advances and Challenges for Therapeutic RNA Editing," Biochemistry, 58: 1947-1957.
Dawson, et al. (2004) J. Biol. Chem., 279(6): 4941-4951.
Diaz et al. (2004) J. Mol. Biol., 342: 971-985.

(Continued)

*Primary Examiner* — Brian Whiteman
(74) *Attorney, Agent, or Firm* — STERNE, KESSLER, GOLDSTEIN & FOX P.L.L.C.

(57) ABSTRACT

RNA editing is achieved using oligonucleotide constructs comprising (i) a targeting portion specific for a target nucleic acid sequence to be edited and (ii) a recruiting portion capable of binding and recruiting a nucleic acid editing entity naturally present in the cell. The nucleic acid editing entity, such as ADAR, is redirected to a preselected target site by means of the targeting portion, thereby promoting editing of preselected nucleotide residues in a region of the target RNA which corresponds to the targeting portion.

19 Claims, 8 Drawing Sheets

Specification includes a Sequence Listing.

(56) References Cited

FOREIGN PATENT DOCUMENTS

| | | |
|---|---|---|
| WO | WO-2016089433 A1 | 6/2016 |
| WO | WO-2017/015555 A1 | 1/2017 |
| WO | WO-2017010556 A1 | 1/2017 |
| WO | WO-2017015575 A1 | 1/2017 |
| WO | WO-2017/050306 A1 | 3/2017 |
| WO | WO-2017062862 A2 | 4/2017 |
| WO | WO-2017/192664 A1 | 11/2017 |
| WO | WO-2017192679 A1 | 11/2017 |
| WO | WO-2017198775 A1 | 11/2017 |
| WO | WO-2017/220751 A1 | 12/2017 |
| WO | WO-2018/041973 A1 | 3/2018 |
| WO | WO-2018/134301 A1 | 7/2018 |
| WO | WO-2019/005884 A1 | 1/2019 |
| WO | WO-2019/158475 A1 | 8/2019 |
| WO | WO-2019/191232 A2 | 10/2019 |
| WO | WO-2019/219581 A1 | 11/2019 |
| WO | WO-2020/252376 A1 | 12/2020 |

OTHER PUBLICATIONS

International Search Report for PCT/EP2017/065467, dated Sep. 15, 2017 (5 pages).
International Search Report for PCT/EP2017/071912, dated Dec. 15, 2017 (5 pages).
International Search Report for PCT/EP2018/051202, dated Mar. 19, 2018 (6 pages).
International Search Report for PCT/EP2019/053291, dated Jun. 6, 2019 (6 pages).
International Search Report for PCT/EP2019/062163, dated Jul. 31, 2019 (6 pages).
International Search Report for PCT/US2020/037580 dated Oct. 2, 2020 (5 pages).
Iwamoto, et al. (2017) Nature Biotech., 35(9): 845-851.
Juliano (2016) "The delivery of therapeutic oligonucleotides," Nucleic Acid Research, 44: 6518-6548.
Kumar et al. Microbiology and Molecular Biology Reviews, vol. 62, p. 1415-1434 (Year: 1998).
Matthews et al. (2016) "Structures of Human ADAR2 Bound to dsRNA Reveal Base-Flipping Mechanism and Basis for Site Selectivity," Nat. Struct. Mol. Biol., 23(5): 426-433.
Mei et al. Trends in Pharmaceological Sciences vol. 41, pp. 475-486 (Year: 2020).
Merkle et al. (2019) "Precise RNA editing by recruiting endogenous ADARs with antisense oligonucleotides," Nature Biotechnology, 37: 133-138.
Mizrahi et al. ACS Chem. Bio. supporting information, pp. 1-4 (Year: 2013).
Mizrahi et al. ACS Chem. Biol. 8, 832-839 (Year: 2013).
Montiel-Gonzalez et al. (2016) "An Efficient System for Selectively Altering Genetic Information Within mRNAs," Nucleic Acid Research, 44(21): e157 (12 pages).
Montiel-Gonzalez et al. (2019) "Current strategies for Site-Directed RNA Editing using ADARs," Methods, 156: 16-24.
Nelwan, M. Journal of Advances in Biology & Biotechnology 16(3): 1-12 (Year: 2017).
Rutten et al. Brain 139: 1123-1135 (Year: 2016).
Schneider et al. (2014) "Supporting Information: Optimal GuideRNAs for Re-directing Deaminase Activity of hADAR1 and hADAR2 in Trans," URL: http://nar.oxfordjournals.org/content/suppl/2014/04/05/gku272.DC1/nar-03496-met-g-2013-File007.pdf (15 pages).
Search Report for GB1700939.0, dated Oct. 1, 2017 (2 pages).
Singleton et al. (1999) Structure, 7(3): 237-244.
Stafforst et al. (2012) "Supporting Information: An RNA-deaminase Conjugate Selectively Repairs Point Mutations," URL: PQR-013_ https://onlinelibrary.wiley.com/action/downloadSupplement?doi=10.1002%2Fanie.201206489&file=anie 201206489_sm_miscellaneous_information.pdf (23 pages).
Turunen, "Axiomer Technology. Therapeutic oligonucleotides for directing site-specific A-to-I editing by endogenous ADAR enzymes," Sep. 25, 2017 (Retrieved from https://www.proqr.com/wp-content/uploads/downloads/2017/11/Axiomer%20technology%20OTS%20170921.pdf) (22 pages).
UKIPO Search Report for GB1808146.3, dated Jan. 30, 2019 (5 pages).
Vogel et al. (2014) ChemMedChem, 9(20):2021-2025.
Written Opinion for PCT/EP2017/065467, dated Sep. 15, 2017 (5 pages).
Written Opinion for PCT/EP2017/071912, dated Dec. 15, 2017 (5 pages).
Written Opinion for PCT/EP2018/051202, dated Mar. 19, 2018 (7 pages).
Written Opinion for PCT/EP2019/053291, dated Jun. 6, 2019 (5 pages).
Written Opinion for PCT/EP2019/062163, dated Jul. 31, 2019 (6 pages).
Written Opinion for PCT/US2020/037580, dated Oct. 2, 2020 (7 pages).
Yang et al. (2006) "Artificially expanded genetic information system: a new base pair with an alternative hydrogen bonding pattern," Nucleic Acid Research, 34(21): 6095-6101.
Zangemeister-Wittke et al. (2000) Clinical Cancer Research, 6(6):2547-2555.
Zheng et al. (2017) Nucleic Acids Research, 45(6):3369-3377.
Zhou et al. (2009) Proteins, 76(1): 151-163.
Aruscavage et al. (2000) "A phylogenetic analysis reveals an unusual sequence conservation within introns involved in RNA editing," RNA, 6(2):257-69.
Grünewald et al. (2014) "Does uncoupling protein 2 expression qualify as marker of disease status in LRRK2-associated Parkinson's disease," Antioxid. Redox Signal., 20(13):1955-60.
Hallegger et al. (2006) "RNA aptamers binding the double-stranded RNA-binding domain," RNA., 12(11):1993-2004.
International Search Report for PCT/EP2015/080347, dated Apr. 1, 2016 (5 pages).
Lamond et al. (1993) "Antisense oligonucleotides made of 2'-O-alkylRNA: their properties and applications in RNA biochemistry," FEBS Lett., 325(1-2):123-7.
Lancaster et al. (2014) "Organogenesis in a dish: modeling development and disease using organoid technologies," Science, 345(6194):1247125.
Masliah et al. (2013) "RNA recognition by double-stranded RNA binding domains: a matter of shape and sequence," Cell Mol. Life Sci., 70(11):1875-95.
Montiel-Gonzalez et al. (2013)"Correction of mutations within the cystic fibrosis transmembrane conductance regulator by site-directed RNA editing," Proc. Natl Acad. Sci. USA, 110(45):18285-90.
Papkovskaia et al. (2012) "G2019S leucine-rich repeat kinase 2 causes uncoupling protein-mediated mitochondrial depolarization," Hum. Mol. Genet., 21(19):4201-13.
Saccomanno et al. (1999) "A minor fraction of basic fibroblast growth factor mRNA is deaminated in *Xenopus* stage VI and matured oocytes," RNA, 5: 39-48.
Sala et al. (2009) "Tissue-engineered small intestine and stomach form from autologous tissue in a preclinical large animal model," J Surg. Res., 156(2):205-12.
Sato et al. (2011) "Long-term expansion of epithelial organoids from human colon, adenoma, adenocarcinoma, and Barrett's epithelium," Gastroenterology, 141(5):1762-72.
Schade et al. (1999) "A 6 bp Z-DNA hairpin binds two Zα domains from the human RNA editing enzyme ADAR1," FEBS Lett., 458(1):27-31.
Schneider et al. (2014) "Optimal guide RNAs 1-29 for re-directing deaminase activity of hADAR1 and hADAR2 in trans," Nucleic Acids Res., 42(10):e87-e87.
Score result to Fukuoka University 2015. (Year: 2015).
Score result to Lavanon et al. WO2005-087949. (Year: 2005).
Score result to Masatora et al. 2015. (Year: 2015).
Sharma et al. (2015) "Oligonucleotide Therapeutics: Chemistry, Delivery and Clinical Progress," Future Med. Chem., 7(16): 2221-2422.

(56) References Cited

OTHER PUBLICATIONS

Smith et al. (2016) "Fibroblast Biomarkers of Sporadic Parkinson's Disease and LRRK2 Kinase Inhibition," Mol. Neurobiol., 53(8):5161-77.
Stafforst et al. (2012) "An RNA-deaminase Conjugate Selectively Repairs Point Mutations," Angewandte Chemie Int. Ed., 51(44):11166-11169.
Tian et al. (2004) "The double-stranded-RNA-binding motif: interference and much more," Nat. Rev. Mol. Cell Biol., 5(12):1013-23.
Vogel et al. (2014) "Improving site-directed RNA editing in vitro and in cell culture by chemical modification of the guideRNA," Angew Chem Int Ed Engl., 53(24):6267-71.
Woolf et al. (1995) "Toward the therapeutic editing of mutated RNA sequences," Proc. Natl. Acad. Sci. USA, 92(18):8298-83.
Written Opinion for PCT/EP2015/080347, dated Apr. 1, 2016 (5 pages).
Stefl et al. (2006) "Structure and Specific RNA Binding of ADAR2 Double-Stranded RNA Binding Motifs," Structure 14(2): 345-355.
Tian et al. (2011) "A Structural Determinant Required for RNA Editing," Nucleic Acids Res. 39(13): 5669-5681.
Agrawal, S., et al., "Mixed-Backbone Oligonucleotides Containing Phosphorothioate and Methylphosphonate Linkages as Second Generation Antisense Oligonucleotide," Nucleosides & Nucleotides 16(7-9):927-936, Taylor & Francis, United Kingdom (Jul. 1997).
Agrawal, S., et al., "Mixed-backbone oligonucleotides as second generation antisense oligonucleotides: in vitro and in vivo studies," Proc. Natl. Acad. Sci. USA 94:2620-2625, National Academy of Sciences, United States (Mar. 1997).
Allain, F.H., et al., "Structural basis of the RNA-binding specificity of human U1A protein," Embo J. 16(18):5764-5774, European Molecular Biology Organization, Germany (Sep. 1997).
Burkard, M.E., and Turner, D.H., "NMR Structures of r(GCAGGCGUGC)2 and Determinants of Stability for Single Guanosine-Guanosine Base Pairs," Biochemistry 39:11748-11762, American Chemical Society, United States (Sep. 2000).
Deleavey, G.F., and Damha, M.J., "Designing Chemically Modified Oligonucleotides for Targeted Gene Silencing," Chemistry & Biology 19(8):937-954, Cell Press, United States (Aug. 2012).
Desterro, J.M., et al., "Dynamic association of RNA-editing enzymes with the nucleolus," J. Cell Sci. 116(9): 1805-1818, The Company of Biologists, United Kingdom (May 2003).
Eggington, J.M., et al., "Predicting sites of ADAR editing in double-stranded RNA," Nature Communications 2(1):1-9, Nature Publishing Group, Germany (May 2011).
Garncarz, W., et al., "A high-throughput screen to identify enhancers of ADAR-mediated RNA-editing," RNA Biology 10(2):192-204, Landes Bioscience, United States (Feb. 2013).
Hamma, T., and Miller, P.S., "Syntheses of alternating oligo-2'-O-methylribonucleoside methylphosphonates and their interactions with HIV TAR RNA," Biochemistry 38(46):15333-15342, American Chemical Society, United States (Nov. 1999).
Haudenschild, B.L., et al., "A transition state analogue for an RNA-editing reaction," J. Am. Chem. Soc. 126(36):11213-11219, American Chemical Society, United States (Sep. 2004).
Higuchi, M., et al., "RNA editing of AMPA receptor subunit GluR-B: a base-paired intronexon structure determines position and efficiency," Cell 75:1361-1370, Cell Press, United States (Dec. 1993).
Ikehara, M., et al., "Nucleosides and nucleotides. XLVII. Conformation of purine nucleosides and their 5'-phosphates" Biochemistry 11(5):830-836, American Chemical Society, United States (Feb. 1972).
Jiang, F., et al., "Structural basis of RNA folding and recognition in an AMP-RNA aptamer complex," Nature 382:183-186, Nature Publishing Group, Germany Jul. 1996.
Juliano, R.L., et al., "Cellular Uptake and Intracellular Trafficking of Antisense and siRNA Oligonucleotides," Bioconjug. Chem. 23(2):147-157, American Chemical Society, United States (Feb. 2012).

Kean, J.M., et al., "Inhibition of Herpes Simplex Virus Replication by Antisense Oligo-2'-O-methylribonucleoside Methylphosphonates," Biochemistry 34(45): 14617-14620, American Chemical Society, United States (Nov. 1995).
Kuttan, A., and Bass, B.L., et al., "Mechanistic insights into editing-site specificity of ADARs," Proc. Natl. Acad. Sci. USA 109(48):E3295-E3304, National Academy of Sciences, United States (Nov. 2012).
Penn, A.C., et al., "Steric antisense inhibition of AMPA receptor Q/R editing reveals tight coupling to intronic editing sites and splicing," Nucleic Acids Res. 41(2):1113-1123, Oxford Academic Press, United Kingdom (Jan. 2013).
Lennox, K. A., and Behlke, M. A., "Chemical modification and design of anti-miRNA oligonucleotides," Gene Therapy 18(12):1111-1120, Nature Publishing Group, United Kingdom (Dec. 2011).
Lomeli, H., et al., "Control of kinetic properties of AMPA receptor channels by nuclear RNA editing," Science 266(5191):1709-1713, American Association for the Advancement of Science, United States (Dec. 1994).
Lu, J., et al., "Synthesis of pyridine, pyrimidine and pyridinone C-nucleoside phosphoramidites for probing cytosine function in RNA," J. Org. Chem. 74:8021-8030, American Chemical Society, United States (Nov. 2009).
MacBeth, M.R., et al., "Evidence for auto-inhibition by the N terminus of hADAR2 and activation by dsRNA binding," RNA 10:1563-1571, Cold Spring Harbor Laboratory Press, United States (Oct. 2004).
MacBeth, M.R., and Bass, B.L., "Large-scale overexpression and purification of ADARs from *Saccharomyces cerevisiae* for biophysical and biochemical studies," Methods Enzymol. 424:319-331, Elsevier, Netherlands (Jan. 2007).
Matsui, M., et al., "Effect of 2'-O-methyl/thiophosphonoacetate-modified antisense oligonucleotides on huntingtin expression in patient-derived cells," Artificial DNA: PNA & XNA 5(3):e11463911-e11463915, Taylor & Francis, United Kingdom (Dec. 2014).
Maydanovych, O., et al., "Probing adenosine-to-inosine editing reactions using RNA-containing nucleoside analogs," Methods in Enzymology 424:369-386, Elsevier, Netherlands (Jan. 2007).
Murayama, K., et al., "Highly stable duplex formation by artificial nucleic acids acyclic threoninol nucleic acid (aTNA) and serinol nucleic acid (SNA) with acyclic scaffolds," Chem. Eur. J. 19:14151-14158, Wiley-VCH Verlag, Germany (Oct. 2013).
Nishikura, K., "Functions and regulation of RNA editing by ADAR deaminases,"Annu. Rev. Biochem. 79:321-349, Annual Reviews, United States (Oct. 2010).
Pan, B., et al., "Crystal Structure of an RNA 16-mer Duplex R(GCAGAGUUAAAUCUGC)2 With Nonadjacent G(Syn)A+(Anti) Mispairs," Biochemistry 38(9):2826-2831, American Chemical Society, United States (Mar. 1999).
Pasternak, A., and Wengel, J., "Unlocked nucleic acid—an RNA modification with broad potential," Org. Biomol. Chem. 9:3591-3597, Royal Society of Chemistry, United Kingdom (Mar. 2011).
Rieder, L.E., et al., "Tertiary structural elements determine the extent and specificity of messenger RNA editing," Nature Communications 4:2232, Nature Publishing Group, United Kingdom (Aug. 2013).
Schweitzer, M., and Engels, J.W., "Sequence specific hybridization properties of methylphosphonate oligodeoxynucleotides," J. Biomol. Struct. Dyn. 16(6):1177-1188, Taylor & Francis, United Kingdom (Jun. 1999).
Sheehan, D., et al., "Biochemical properties of phosphonoacetate and thiophosphonoacetate oligodeoxyribonucleotides," Nucleic Acids Research 31(14):4109-4118, Oxford Academic Press, United Kingdom (Jul. 2003).
Sipova, H., et al., "5'-O-Methylphosphonate nucleic acids—new modified DNAs that increase the *Escherichia coli* RNase H cleavage rate of hybrid duplexes," Nucleic Acids Research 42(8):5378-5389, Oxford Academic Press, United Kingdom (Apr. 2014).
Stefl, R., et al., "A novel RNA pentaloop fold involved in targeting ADAR2," RNA 11(5):592-597, Cold Spring Harbor Laboratory, United States (May 2005).

(56) References Cited

OTHER PUBLICATIONS

Svoboda, P., et al., "Hairpin RNA: a secondary structure of primary importance," Cell Mol. Life Sci. 63(7):901-908, Birkhauser Verlag, Switzerland (Apr. 2006).

The Glen Report, "Phosphonoacetate (PACE) Oligonucleotides," Glenesearch.com, vol. 20, No. 2, Oct. 2008, accessed at https://www.glenresearch.com/media/contentmanager/content/glemeport/GR20-2.pdf, accessed on Dec. 8, 2022, 16 pages.

Vaish, N., et al., "Improved specificity of gene silencing by siRNAs containing unlocked nucleobase analogs," Nucleic Acids Res. 39(5):1823-1832, Oxford Academic Press, United Kingdom (Mar. 2011).

Veliz, E.A., et al., "Substrate analogues for an RNA-editing adenosine deaminase: mechanistic investigation and inhibitor design," J. Am. Chem. Soc., 125(36):10867-10876, American Chemical Society, United States (Sep. 2003).

Wong, S.K., et al., "Substrate recognition by ADAR1 and ADAR2," RNA 7:846-858, Cold Spring Harbor Laboratory, United States (Jun. 2001).

Savva, Y.A., et al. "The ADAR protein family," Genome Biology 13:252, BioMed Central, United States (Dec. 2012).

\* cited by examiner

TARGETED RNA EDITING

RELATED APPLICATIONS

This application is a continuation of U.S. patent application Ser. No. 15/531,164, which has a 371(c) date of May 26, 2017, and is a § 371 National Stage Application of PCT/EP2015/080347, filed Dec. 17, 2015, which claims priority to and the benefit of United Kingdom patent applications 1422511.4, filed Dec. 17, 2014, 1512467.0, filed Jul. 16, 2015, 1512595.8, filed Jul. 17, 2015, and 1521987.6, filed Dec. 14, 2015 respectively), the complete contents of each of which are hereby incorporated herein by reference for all purposes.

REFERENCE TO SEQUENCE LISTING SUBMITTED ELECTRONICALLY

The content of the electronically submitted sequence listing in ASCII text file (Name 4430_0060005_Sequence_Listing_ST25.txt; Size: 19,896 bytes; and Date of Creation: Mar. 13, 2023) filed with the application is incorporated herein by reference in its entirety.

TECHNICAL FIELD

The invention is in the field of RNA editing, whereby the nucleotide sequence of a target RNA sequence is modified e.g. to correct a mutation.

BACKGROUND ART

RNA editing is a natural process through which eukaryotic cells alter the sequence of RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms, such as *Caenorhabditis elegans*, to humans. Examples of RNA editing are adenosine to inosine and cytidine to uridine conversions through enzymes called adenosine deaminase and cytidine deaminase, respectively. The most extensively studied RNA editing system is the adenosine deaminase enzyme. Adenosine deaminase is a multidomain protein, comprising a recognition domain and a catalytic domain. The recognition domain recognizes a specific dsRNA sequence and/or conformation, whereas the catalytic domain converts an adenosine into inosine in a nearby, more or less predefined, position in the target RNA, by deamination of the nucleobase. Inosine is read as guanine by the translational machinery of the cell, meaning that, if an edited adenosine is in a coding region of a mRNA or pre-mRNA, it can recode the protein sequence. A to I conversion may also occur in 5' non-coding sequence of a target mRNA, creating new translational start sites upstream of the original start site, which gives rise to N-terminally extended proteins. In addition, A to I conversions may take place in splice elements in introns or exons in pre-mRNAs, thereby altering the pattern of splicing. Exons may be included or skipped, as a consequence of such RNA editing. The adenosine deaminases are part of the extensive family of enzymes called adenosine deaminases acting on RNA (ADAR), including human deaminases hADAR1, hADAR2 and hADAR3.

The use of oligonucleotides to edit a target RNA is known in the art, e.g. see Montiel-Gonzalez et al. (Proceedings of the National Academy of Sciences 2013 Nov. 5, 2013, vol. 110, no. 45, pp. 18285-18290). The authors described the targeted editing of a target RNA using a genetically engineered fusion protein, comprising an adenosine deaminase domain of the hADAR1 protein, fused to the so-called B-box binding domain of bacteriophage lambda protein N. The natural recognition domain of hADAR1 had been removed to eliminate the substrate recognition properties of the natural ADAR and replace it by the B-box recognition domain of lambda N-protein. The B-box is a short stretch of RNA of 17 nucleotides that is recognized by the N-protein B-box binding domain. The authors created an antisense oligonucleotide comprising a guide RNA part that is complementary to the target sequence for editing fused to a B-box portion for sequence specific recognition by the N-domain-deaminase fusion protein. The authors elegantly showed that the guide RNA oligonucleotide faithfully directed the adenosine deaminase fusion protein to the target site, resulting in gRNA-directed site-specific A to I editing of the target RNA.

A disadvantage of the proposed method is the need for a fusion protein consisting of the B-box binding domain of bacteriophage lambda N-protein, genetically fused to the adenosine deaminase domain of a truncated natural ADAR protein. This requires the target cells to be either transduced with the fusion protein, which is a major hurdle, or that the target cells are transfected with a nucleic acid construct encoding the engineered adenosine deaminase fusion protein for expression in the target cells. The latter constitutes no minor obstacle when editing is to be achieved in a multicellular organism, such as in therapy against human disease.

Vogel et al. (Angewandte Chemie. Int. Ed. 2014, 53, 6267-71) disclose editing of eCFP and Factor V Leiden coding RNAs using a benzylguanine substituted guideRNA and a genetically engineered fusion protein, comprising the adenosine deaminase domains of ADAR1 or 2 genetically fused to a SNAP-tag domain (an engineered O6-alkylguanine-DNA-alkyl transferase). Although the genetically engineered artificial deaminase fusion protein could be targeted to a desired editing site in the target RNAs in Hela cells in culture, using covalently linked guide RNA (through benzylguanine), this system suffers from similar drawbacks as the genetically engineered ADARs described above, in that it is not clear how to apply the system without having to genetically modify the ADAR first and subsequently transfect or transduct the cells harboring the target RNA, to provide the cells with this genetically engineered protein. Clearly, this system is not readily adaptable for use in humans, e.g. in a therapeutic setting.

Another editing technique which uses oligonucleotides is known as CRISPR/Cas9 system, but this editing complex acts on DNA. The latter method suffers from the same drawback as the engineered ADAR systems described above, as it requires co-delivery to the target cell of the CRISPR/Cas9 enzyme, or an expression construct encoding the same, together with the guide oligonucleotide.

Hence, there remains a need for new techniques which can utilise endogenous cellular pathways to edit endogenous nucleic acids in mammalian cells, even in whole organisms, without the problems associated with the methods of the prior art.

DISCLOSURE OF THE INVENTION

The present invention does away with the drawbacks of the methods according to the prior art by providing a targeted approach to RNA editing using oligonucleotide constructs comprising a targeting portion specific for the target nucleic acid sequence to be edited and a recruiting portion capable of binding and recruiting a nucleic acid editing entity naturally present in the cell. The function of the recruiting portion of the oligonucleotide construct is to selectively bind with sufficient affinity to a RNA editing entity endogenous to and resident in the cell, redirecting such entity to a preselected target site by means of the targeting portion of the oligonucleotide construct of the invention, thereby promoting the editing of preselected nucleotide residues in a region of the target RNA corresponding to the targeting portion of the oligonucleotide construct.

The targeting portion of the oligonucleotide construct usually comprises an antisense oligonucleotide sequence that is complementary to the target site in the RNA sequence to be edited. One preferred embodiment of such a targeted approach for editing target RNA is an oligonucleotide construct comprising two portions, a targeting portion, comprising an antisense sequence complementary to the target RNA sequence, and a recruiting portion comprising a recognition sequence for an RNA editing enzyme.

The recruiting portion may comprise a dsRNA in the form of a hairpin structure, with a stem and a loop. The hairpin may reside upstream (5') or downstream (3') of the targeting portion (preferably upstream). Alternatively, the recruiting portion of the oligonucleotide construct may interrupt the targeting portion in such a way that part of the targeting portion lies upstream of the recruiting portion and part of the targeting portion lies downstream of the recruiting portion, causing the recruiting portion of the oligonucleotide construct to loop out after the oligonucleotide construct anneals to the target RNA.

According to another embodiment, the recruiting portion comprises a dsRNA segment that mimics, i.e. is identical or similar in structure to, an RNA sequence known to be edited by naturally occurring RNA editing entities. This RNA sequence known to be a natural substrate for RNA editing comprises a dsRNA segment, preferably comprising a single RNA segment that folds back upon itself through complementary nucleobase pairing, thereby forming a hairpin or stem-loop structure. Two examples of known edited RNA sequences that have been characterised in great detail are in the B-subunit of the 3-amino-3-hydroxy-5-methyl-4-isoxazole propionic acid (AMPA) subtype glutamate receptor (GluR-B). This model system comprises two frequently edited sites wherein DNA encoded AGA is edited to IGA, resulting in an arginine-to-glycine substitution (R/G site) and a distinct glutamine-to-arginine substitution (Q/R site). The GluR-B (R/G) site is known to comprise of a stem-loop structure consisting of 71 nucleotides comprising 3 mismatches, 2 A·C and one G·U wobble base pairs. Interestingly, the loop consists of a well conserved pentaloop structure GCUAA structure that conforms to a phylogenetically conserved GCUMA sequence, wherein M is A or C (Aruscavage P. J. & Bass B. L. RNA. 2000; 6: 257-269). There seems to be some preference for editing of the two wobble adenosines, with an increasing efficiency when the base opposite the edited adenosine is selected from cytidine or uridine, cytidine being preferred.

This structure may conveniently be used as is, or be adapted when used in an oligonucleotide construct according to the invention, as a recruiting portion, by reducing or increasing the number of wobble nucleobase pairs in the stem to modify the specificity of editing and/or redirect editing to preferred site(s) in the target RNA sequence. In addition, or alternatively, the recognition site of the GluR-B for hADAR1 may be modified by shortening the stem without abolishing the recognition altogether. Such shortening may be convenient from a manufacturability or cost of good perspective, and the like.

An example of a recruiting portion derived from the GluR-B domain comprises the sequence: 5'-(AUA$N^a$)$_n$U-AUAACAAUAUgcuaaAUGUUGUUAUA($N^b$UAU)$_n$-3' (SEQ ID NO:47), wherein $N^a$ and $N^b$ are each single nucleotides which may be A, G, C or U, with the proviso that $N^a$ and $N^b$ form a mismatch base pair upon the formation of a stem-loop structure, and n is 1 or 0 (i.e. SEQ ID NOs: 6 & 7). A useful example of such a recruiting portion includes this sequence where n=1, with further extensions in the 5' and 3' directions e.g. where each extension is from 1 to 10 nucleotides long (or longer e.g. 1 to 20 nucleotides or more). For instance, extending 3 further nucleotides in each direction gives (SEQ ID NO: 23) 5'-GGAAUA-$N^a$UAUAACAAUAUgcuaaAUGUUGUUAUA$N^b$UAUCCC-3', as seen within SEQ ID NOs: 20-22 (in which $N^a$=$N^b$=G). This further extension may improve correction efficiency.

Another example of a recruiting portion based on full-length natural GluR-B receptor substrate is 5'-GUGGAAUA$N^a$UAUAACAAUAUgcuaaAUGUUGUUAUAN$^b$UAUCCCAC-3' (SEQ ID NO: 24; extended sequence relative to preceding paragraph underlined), as used below in the Examples. The full-length GluR-B receptor recruiting portion in combination with targeting portions for the A1AT-transcript with the G to A mutation in position 9989 associated with A1AT-deficiency is described in Example 4. The full-length GluR-B receptor recruiting portion in combination with targeting portions for the LRRK2 transcript with the G2019S mutation, associated with Parkinson's disease, is described in Example 5.

The recruiting portion may be linked at the 5' or 3' end to a targeting portion, optionally via a linker "L" that comprises one or more nucleotides, an oligopeptide or another chemical linker, such as polyethylene glycol (PEG).

The targeting portion may comprise a sequence that is complementary to the target RNA sequence represented by the general formula:

(SEQ ID NO: 8)
$N^1N^2N^3N^4N^5N^6N^7N^8N^9N^{10}N^{11}N^{12}N^{13}N^{14}N^{15}N^{16}N^{17}CN^{18}N^{19}N^{20}$, wherein $N^1$ to $N^{20}$, depending on the complementary sequence in the target RNA sequence, each independently are A, G, C or U, wherein $N^4$ preferably forms a mismatch base pair with its opposing nucleotide in the target RNA sequence when the targeting portion is annealed to its target RNA sequence, and $N^{10}$ and $N^{16}$ form wobble base pairs with their opposing nucleotide in the target RNA sequence when the targeting portion is annealed to its target RNA sequence, and C is cytidine opposite the adenosine in the target RNA sequence that is a target for deamination.

Mismatch basepairs are G-A, C-A, U-C, A-A, G-G, C-C, U-U basepairs. Wobble base pairs are: G-U, I-U, I-A, and I-C basepairs. The targeting portion may be longer than 20 nucleotides, as much as 200 nucleotides or more, although it is believed that longer than 50 is not necessary, and shorter than 40 is preferred. Still more preferred are recruiting portions shorter than 30 nucleotides, preferably shorter than 25 nucleotides.

Preferably, the targeting portion comprises 2'-O methyl groups in each position which opposes an adenosine when the targeting portion is annealed to the target RNA sequence if that adenosine in the target RNA sequence is not a target for editing. More generally, to protect the targeting portion from degradation by nucleases it is preferred that all nucleotides comprise 2'-O-methyl groups, except for the nucleotide opposite the target adenosine and said opposite nucleotide's neighbouring nucleotides (one 5' and one 3'), which should comprise 2'-OH groups.

According to a preferred embodiment, the recruiting portion comprises a DNA sequence: $(CG)_3N^1$-$N''(CG)_3$, (SEQ ID NO:44) wherein each of $N^1$ to $N''$ may be the same or different and selected from guanosine, adenosine, thymidine, cytidine and inosine, 'n' is between 2 and 20, preferably between 2 and 10, more preferably between 2 and 5, still more preferably between 3 and 5, most preferably 4 or 5. Thus there are three CG repeats flanking up to 20 intermediate nucleotides. This DNA sequence is capable of forming a stem-loop structure. According to a further preferred embodiment, the recruiting portion of the oligonucleotide construct is a DNA structure comprising the sequence: $(CG)_3T_n(CG)_3$ (SEQ ID NO:45), wherein n is an integer from 3-5, preferably 4, (CGCGCGTTTTCGCGCG; SEQ ID NO: 5). This DNA sequence is capable of forming a stem-loop structure. Moreover, it has been described in the art that the $(CG)_3T_4(CG)_3$ (SEQ ID NO:5) sequence forms a Z-DNA conformation under physiological conditions and that this Z-DNA structure is recognised and bound by hADAR1 (FEBS letters 458:1 1999 Sep. 10 pg 27-31). As above for the dsRNA recruiting portion, this Z-DNA recruiting portion may lie upstream or downstream of the targeting portion, or interrupt the targeting portion separating the targeting portion in an upstream segment and a downstream segment, whereby the DNA recruiting portion loops out when the targeting portions anneal to the target RNA. According to this embodiment, the cytidine bases are preferably 5-methylcytidine, to reduce potential immunogenicity associated with CpG sequences.

The oligonucleotides according to the present invention comprise a targeting portion (i.e. a portion that targets the oligonucleotide to the correct position in the target RNA sequence) and a recruiting portion (i.e. a portion that has as primary function to recruit the editing entity, e.g. an ADAR, and is not necessarily complementary, preferably not complementary, with the target RNA in the region of the adenosine(s) that are the target(s) for editing). This bipartite structure clearly distinguishes oligonucleotides of the invention from known oligonucleotides such as those disclosed in the prior art (e.g. WO2014/011053, WO2005/094370, and Woolf et al, 1995. PNAS USA 92, 8298-8302) which are essentially complementary to the target over their entire length, and do not comprise a recruitment portion (certainly not one that is not complementary to the target RNA, but instead has affinity for the editing entity, as with the present invention). It is therefore preferred according to the invention to provide an oligonucleotide construct for the site-directed editing of a nucleotide in a target RNA sequence in a eukaryotic cell, said oligonucleotide construct comprising:

(a) a targeting portion, comprising an antisense sequence complementary to part of the target RNA; and (b) a recruiting portion that is not complementary to the target RNA sequence and is capable of binding and recruiting an RNA editing entity naturally present in said cell and capable of performing the editing of said nucleotide.

In accordance with a further embodiment, the invention provides an oligonucleotide construct comprising:

(a) a targeting portion, comprising an antisense sequence complementary to part of the target RNA; and (b) a recruiting portion that is capable of forming an intramolecular stem loop structure, of binding and recruiting an RNA editing entity naturally present in said cell, and of performing the editing of said nucleotide.

According to yet another embodiment, the recruiting portion may be an aptamer selected for binding to the editing entity resident in the cell. Procedures to select aptamers are well known in the art. Aptamers that bind to the editing entity without abolishing the deaminase activity can be selected as recruiting portion and readily fused to the targeting portion of the oligonucleotide construct according to the invention, using any type of linker including regular (phosphodiester) or modified (e.g. phosphorothioate or phosphorodithioate) internucleosidic linkage, peptidyl linkage, or any other chemical linkage, such as polyethylene glycol.

According to yet another embodiment of the invention, an antibody, antibody fragment, binding domain thereof, or a camelid antibody, that binds to an editing entity resident in the cell without abolishing the editing activity, may be selected as a recruiting portion and fused to the targeting portion of the oligonucleotide construct according to the invention.

The term "oligonucleotide construct" may refer to a single oligonucleotide, a complex of two or more oligonucleotides (including an aptamer) with affinity to each other (antisense complementarity or otherwise), or a complex of an oligonucleotide and a proteinaceous binding portion (such as an antibody, antibody fragment or binding domain), which may be linked directly or via a PEG or other linker.

Thus, the present invention provides oligonucleotide constructs and methods for site specific editing of target RNA sequences in a cell, without the need to transduce or transfect the cell with genetically engineered editing enzymes. Due to the design of the oligonucleotide constructs the editing entities, such as ADARs, are recruited and directed to editing sites chosen by the experimenter. These oligonucleotide constructs and methods of the invention can conveniently be used to make changes in target RNA sequences, for example to reverse mutations that are involved in, or cause, disease, thereby alleviating the symptoms of the disease. The RNA editing entities are known to edit their substrates very efficiently, with frequencies far exceeding oligonucleotide mediated DNA or RNA repair. This is of great advantage when used in treating disease.

The targeting portion and the recruiting portion in an oligonucleotide construct according to the invention may be directly adjacent. Alternatively, the targeting portion and the recruiting portion may be linked covalently through a linker. The linker may comprise non-specific nucleotide residues (non-specific in the sense that they are not necessarily complementary to the target RNA sequence nor have affinity to an editing entity resident in the cell), (oligo)peptide linkers, or other chemical linkers. According to yet another embodiment, the targeting portion and the recruiting portion may be provided as two separate—i.e. non-covalently linked—oligonucleotide sequences comprising antisense complementarity capable of forming a dsRNA or a hybrid DNA:RNA structure. The formation of such dsRNA or hybrid oligonucleotide construct may take place prior to administration to the cell or the subject to be treated, or after administration of the two separate oligonucleotides, in vitro, or in vivo, e.g. in the subject to be treated.

The invention provides a method for making a change in a target RNA sequence in a eukaryotic, preferably a mammalian cell, comprising steps of: (i) introducing into said cell an oligonucleotide construct comprising a targeting portion, which comprises a sequence that is sufficiently complementary to the target RNA sequence to bind by nucleobase pairing to said target RNA and a recruiting portion, that comprises a sequence that is recognised by an RNA editing entity that is naturally present in said eukaryotic, preferable mammalian, cell; (ii) allowing sufficient time for the RNA editing entity to perform an editing reaction on the target RNA sequence; and (iii) identifying the presence of the change in the RNA sequence. According to a preferred embodiment, the editing reaction is carried out by said editing entity on one or more nucleobases within the region of overlap between the target RNA sequence and the targeting portion of the oligonucleotide construct. According to a preferred embodiment, the targeting portion of the oligonucleotide construct comprises a mismatch opposite the nucleobase(s) to be edited. According to a further preferred embodiment the editing reaction comprises an A to I conversion by deamination of the adenosine nucleobase in the target RNA sequence. Preferred in accordance with the latter method is one wherein the oligonucleotide construct comprises a C opposite the adenosine to be edited. According to another preferred method, the editing reaction is a C to U conversion through deamination of the cytidine nucleobase; it is preferred in accordance with the latter method that the targeting portion of the oligonucleotide construct comprises an A opposite the C in the target RNA sequence to be edited.

The invention also provides a method for editing a mutant CFTR target RNA sequence in a human cell, comprising steps of: (i) introducing into said cell an oligonucleotide construct comprising a targeting portion that is complementary to the CFTR target RNA sequence and a recruiting portion capable of recruiting a hADAR editing entity; and (ii) allowing sufficient time for the hADAR editing entity to edit nucleobases at or near a region of overlap between the target RNA sequence and the targeting portion of the oligonucleotide construct. In a preferred embodiment according to the invention the mutant CFTR target RNA (a pre-mRNA or mRNA) comprises a G551D mutation, and the editing reaction causes an adenosine to be converted into an inosine thereby reversing the G551D mutation in said target RNA sequence. There are two codons for aspartic acid (D); GAU and GAC. Hence, a cystic fibrosis patient with the G551D mutation may have either mutation GAU or GAC in the position corresponding to codon 551 of the CFTR protein. Deamination of the A in the second position of the codon will lead to formation of an I, which will be read by the translational machinery as a G. Hence, deamination of the A in the second position of the mutated codon creates GIU or GIC, respectively, which are de facto read as GGU and GGC. Both GGU and GGC encode glycine, so that, RNA editing of both mutated G551D codons by an adenosine deaminase will yield a proper glycine encoding triplet, effectively reversing the mutation to a normal CFTR protein.

It will be clear to a person skilled in the art, that the G551D mutation is used as an example only and in no way to limit the scope of the invention. There are literally thousands of genetic diseases caused by single base pair substitutions that are amenable for reversal using oligonucleotide constructs and methods according to the invention, recruiting either a deaminase, such as the adenosine deaminases described in detail herein, or a cytidine deaminase.

The recruitment of cytidine deaminase to a target site works in the same way as for the adenosine deaminases hADAR1 and hADAR2. However, cytidine deaminases have different binding requirements and recognize different structures in their target RNA sequences that determine editing of the cytidine. One particularly well studied cytidine aminase is human Apobec1. The general principle of RNA editing using an oligonucleotide construct to target an editing site and to recruit a resident, naturally present, editing entity remains the same for cytidine deaminases, and is part of the invention disclosed and claimed herein.

DETAILED DESCRIPTION OF THE INVENTION

The oligonucleotide constructs according to the invention are unique in that they combine two essential functions; they bind to naturally present RNA editing entities with a certain affinity and they bind through antisense complementary (Watson-Crick) base pairing to the site in the target RNA sequence where editing is to take place, thereby recruiting the RNA editing entities to the editing site. A "naturally present" entity is present in a cell without the need of prior human intervention. Hence, a truncated or recombinant enzyme (such as described in Montiel-Gonzalez et al., and Vogel et al.) is not naturally present in a cell; they may be present in a cell, but only after human intervention (transduction or transfection). The invention can thus operate using wild-type RNA editing entities which are endogenous to a cell.

It will be understood that such recruiting need not be quantitative, in that all RNA editing entities resident in the cell will be recruited for editing of the target RNA sequence of choice. It is expected, and even considered desirable, if a percentage of resident editing entities remain available to act on their natural substrates. In addition, in certain embodiments, e.g. where the recruiting portion of the oligonucleotide construct is a dsRNA sequence comprising adenosines, the catalytic domain of the RNA editing entity, once recruited by the oligonucleotide construct, may act on the recruiting portion of the oligonucleotide construct, as well as on the editing substrate in the dsRNA portion created by the annealing of the targeting portion to the complementary sequence in the target RNA sequence. This is not a problem under all circumstances, as there may be applications where over-editing is desirable. In cases where over-editing is to be avoided, a targeting portion may be chemically modified in its entirety, for example by providing all nucleotides with a 2'-O-methylated sugar moiety, except in the nucleotide(s) opposite the target adenosine(s) and the two nucleotides (one 5' and one 3') flanking each nucleotide opposing the target adenosine. In general, an adenosine in a target RNA can be protected from editing by providing an opposing nucleotide with a 2'-OMe group, or by providing a guanine or adenine as opposing base, as these two nucleobases are able to prevent editing of the opposing adenosine.

The Oligonucleotide Constructs

The recruiting portion of the oligonucleotide constructs according to the invention are characterized by a dsRNA or dsDNA structure. One way of establishing a double stranded oligonucleotide structure in a single molecule is by establishing a palindromic sequence that is capable of folding back upon itself over at least part of its length. Such stem-loop structures may arise from (1) artificial RNA sequences capable of forming a stem-loop structure, (2) artificial DNA sequences capable of forming a stem-loop structure, (3) RNA sequences taken from known substrate RNAs for editing entities resident in the cell. For example, an oligonucleotide construct according to the invention may comprise a recruiting portion similar in sequence to the natural recognition site for the editing activity, or it may mimic that recognition site in an aptamer-like fashion. Each of these embodiments will be described in more detail below. In addition, those of skill in the art will be capable of making designing and recruiting portions based on each of the embodiments described in greater detail. Methods to design and test nucleic acid structures that have affinity for proteins are, as such, well known in the art.

The targeting portion of an oligonucleotide construct according to the invention should have sufficient overlap and complementarity to the target site to allow for sequence specific hybridisation of the oligonucleotide construct with the target RNA sequence. The length and the amount of overlap may vary from target to target but may be routinely determined by a person having ordinary skill in the art. In general, longer sequences provide more specificity—and consequently fewer off-target effects, e.g. through non-specific binding—and stronger binding to the target site. The targeting portion of the oligonucleotide construct according to the invention should normally be longer than 10 nucleotides, preferably more than 11, 12, 13, 14, 15, 16 still more preferably more than 17 nucleotides. The targeting portion is preferably shorter than 200 nucleotides, more preferably shorter than 100 nucleotides, still more preferably shorter than 50 nucleotides, still more preferable 25 or fewer nucleotides.

According to one embodiment, the invention provides an oligonucleotide construct for making a desired change at one or more specific positions in a target RNA sequence in a cell, by recruiting a RNA editing entity naturally present in said cell, having the sequence 5'-X-(Y-X')$_n$-L-Z-3', wherein X is complementary to the target RNA sequence downstream of the specific position, X' is complementary to the target RNA sequence upstream of the specific position, Y comprises one or more nucleotides (e.g. up to 10, preferably between 1 and 5, more preferably between 1 and 3, such as 1 or 2) which is/are not complementary to the target RNA sequence, n is an integer from 1 to 10 (preferably from 1 to 5, more preferably from 1 to 3, or 1), L is a linker sequence that is optional and may comprise any number of nucleotides including zero, and Z is a sequence that is recognised by and binds to said RNA editing entity. L may also consist of a different chemical linkage, such as a (oligo)peptide linkage, or PEG linkage.

When n is greater than or equal to 1 the targeting portion of the oligonucleotide construct is not perfectly complementary to the target RNA sequence, but instead comprises one or more mismatches, or wobble bases, which serve to enhance the specificity, by increasing the frequency of editing of the opposing nucleotide in the target RNA sequence. When n is two or more, X' occurs more than once and two or more X' may be identical depending on the sequence of the complementary bases in the target RNA sequence, but in all likelihood, the two or more X' are not identical. When n is 0, the targeting portion is perfectly complementary to the target RNA sequence over the entire length of the targeting portion, i.e. without any mismatches, to the target RNA sequence. This embodiment is likely to cause RNA editing by adenosine deaminase in a non-specific way, meaning all adenosines in the overlapping region between target portion of the oligonucleotide construct and the target RNA sequence are equally likely to become converted to inosine. Any non-specific editing of adenosines can be limited, by making sure that the adenosines that should not be targeted, or at least at a lower frequency, encounter an opposite nucleotide with a 2'-O modified ribose moiety, such as a 2'-OMe, as the latter is known to reduce the efficiency of editing of the opposite adenosine. Alternatively, or additionally, an opposing base being a guanine or adenine may be provided, as these nucleobases generally impede deamination of the opposing base.

According to another embodiment, the invention provides an oligonucleotide construct for making a desired change at a specific position in a target RNA sequence in a cell, by recruiting a RNA editing entity naturally present in said cell, having the sequence 5'-Z-L-(X'-Y)$_n$-X-3', wherein X is complementary to the target RNA sequence upstream of the specific position, X' is complementary to the target RNA sequence downstream of the specific position, Y comprises one or more nucleotides which is/are not complementary to the target RNA sequence (e.g. up to 10, preferably from 1 to 5, more preferably from 1 to 3, such as 1 or 2), n is an integer from 1 to 10 (preferably from 1 to 5, more preferably from 1 to 3, or 1), L is a linker sequence that is optional and may comprise any number of nucleotides including zero, and Z is a sequence that is recognised by and binds to said RNA editing entity. L may also consist of a different chemical linkage, such as a (oligo)peptide linkage.

When n is greater than or equal to 1 the targeting portion of the oligonucleotide construct is not perfectly complementary to the target RNA sequence, but instead comprises one or more mismatches, or wobble bases, which serve to enhance the specificity, by increasing the frequency of editing of the opposing nucleotide in the target RNA sequence. When n is two or more, X' occurs more than once and two or more X' may be identical depending on the sequence of the complementary bases in the target RNA sequence, but in all likelihood, the two or more X' are not identical. When n is 0, the targeting portion is perfectly complementary to the target RNA sequence over the entire length of the targeting portion, i.e. without any mismatches, to the target RNA sequence. This embodiment is likely to cause RNA editing by adenosine deaminase in a non-specific way, meaning all adenosines in the overlapping region between target portion of the oligonucleotide construct and the target RNA sequence are equally likely to become converted to inosine. Any non-specific editing of adenosines can be limited, by making sure that the adenosines that should not be targeted, or at least at a lower frequency, encounter an opposite nucleotide with a 2'-O modified ribose moiety, such as a 2'-OMe, as the latter is known to reduce the efficiency of editing of the opposite adenosine.

An oligonucleotide of the invention can be a hybrid DNA/RNA molecule i.e. including both deoxyribo- and ribo-nucleotides within the same oligonucleotide.

Recruiting Portion: Preferred Embodiments

The recruiting portion should be long enough to provide a structure, such as a stem-loop RNA or DNA structure, preferably in the Z-RNA or Z-DNA conformation, that is recognized by the editing entity according to the invention. If the editing entity is hADAR1, nucleic acid sequences are known that provide for recognition and binding by the Z-alpha domain of the 150 kDa variant of hADAR1.

Recruiting Portions from Artificial RNA or DNA Stem-Loop Structures

An example of an artificial RNA or DNA stem-loop structure, being a preferred recruiting portion according to the invention, comprises the sequence (RY or YR)$_n$N$_m$(RY or YR)$_n$, wherein R, Y and N represent either ribonucleotides or desoxyribonucleotides and wherein R is A or G, Y is T, U or C, N is A, G, C, T or U, n is 3 or more, m is 1 or more (preferably m is 2 or more, more preferably m is 3 or more, still more preferably m is 4 or more) and wherein N forms a loop and the two $(RY)_n$ or $(YR)_n$ sequences either form a dsRNA stem structure (when all nucleotides are ribonucleotides) or dsDNA structure (when all nucleotides are desoxyribonucleotides) via complementary Watson-Crick nucleobase pairing. The recruiting portion preferably consists of all ribonucleotides or all desoxyribonucleotides, although a recruiting portion comprising both ribo- and desoxyribonucleotides is not excluded.

Especially preferred examples of recruiting portions known to bind to hADAR1 are (i) the DNA structures represented by $(CG)_nT_m(CG)_n$ (SEQ ID NO:46) wherein n is 3 and m is 4 or more, preferably 4 or 5, which has a tendency to form so-called Z-DNA structures, (ii) RNA structures represented by the formula $(RY)_nN_m(RY)_n$, wherein R is A or G, Y is C or U, N is any A, G, C, or U and wherein N may all be the same or different, n is 3 or more, m is 4 or more, preferably 4 or 5, which has a tendency to form Z-RNA structures. Z-DNA and Z-RNA structures differ from their more common counterparts (for dsDNA the B conformation is the most common form, whereas for dsRNA the A-form is most common) by the fact that the double helix is left-handed as opposed to A and B forms, which are both right-handed, and the nucleobases in the backbone of Z-DNA and Z-RNA are spatially arranged in a zigzag arrangement (hence the prefix "Z").

Recruiting Portions from Natural Substrate RNAs

Non Z-RNA forming dsRNA sequences forming stem-loop structures and bulges also come into play as recruiting portions. Various dsRNA structures, with stem-loops and mismatches or wobble base pairs, other than the GluR-B described in some detail above, have been described in the art that interact with the binding domain of editing entities, such as GluR-C and GluR-D, 5-$HT_{2c}$ serotonine receptors and several pri- and pre-miRNAs and miRNAs. Preferred loops in the recruiting portions of the oligonucleotide constructs according to the invention conform to the tetra- or pentaloop conserved sequences UNCG, wherein N may be any A, G, C or U, or GCUMA, wherein M is A or C, respectively. When the recruiting portion comprises a stem loop segment from a known RNA editing site in the art, the stem may be taken "as is" or may altered in sequence or length, shortened, or modified in some other way, to alter its characteristics, such as affinity for the RNA editing entity, or for reasons of manufacturability or handling, cost, or any other reason, as long as the recruiting function is not entirely impaired. These structures can readily be made in vitro and tested for their ability to bind to, recruit, and redirect editing entities. Several editing entities are known in the art that can be obtained commercially, including hADARs, and tested in assays for binding to dsRNA or dsDNA structures in oligonucleotide constructs according to the invention. Such assays are readily available to those having ordinary skill in the art of protein-nucleic acid interactions, and include an electrophoretic mobility shift assay (EMSA).

Two examples of known edited RNA sequences that have been characterised in great detail are in the B-subunit of the 3-amino-3-hydroxy-5-methyl-4-isoxazole propionic acid (AMPA) subtype glutamate receptor (GluR-B). This model system comprises two frequently edited sites wherein DNA encoded AGA is edited to IGA, resulting in an arginine-to-glycine substitution (R/G site) and a distinct glutamine-to-arginine substitution (Q/R site). The GluR-B (R/G) site is known to comprise of a stem-loop structure consisting of 71 nucleotides comprising 3 mismatches, 2 A·C and one G·U wobble base pairs. Interestingly, the loop consists of a well conserved pentaloop structure GCUAA structure that conforms to a phylogenetically conserved GCUMA sequence, wherein M is A or C (Aruscavage P. J. & Bass B. L. RNA. 2000; 6: 257-269). There seems to be some preference for editing of the two wobble adenosines, with an increasing efficiency when the base opposite the edited adenosine is selected from cytidine or uridine, cytidine being preferred.

This structure may conveniently be used as is, or be adapted when used in an oligonucleotide construct according to the invention, as a recruiting portion, by reducing or increasing the number of wobble nucleobase pairs in the stem to modify the specificity of editing and/or redirect editing to preferred site(s) in the target RNA sequence. In addition, or alternatively, the recognition site of the GluR-B for hADAR1 may be modified by shortening the stem without abolishing the recognition altogether. Such shortening may be convenient from a manufacturability or cost of good perspective, and the like.

An example of a recruiting portion derived from the GluR-B domain, being a preferred embodiment according to the invention, comprises the sequence: 5'-$(AUAN^a)_n$U-AUAACAAUAUgcuaaAUGUUGUUAUA($N^bUAU)_n$-3' (SEQ ID NO:47), wherein $N^a$ and $N^b$ are each single nucleotides which may be A, G, C or U, with the proviso that $N^a$ and $N^b$ form a mismatch base pair upon the formation of a stem-loop structure, and n is 1 or 0 SEQ ID NOs: 6 & 7).

Another preferred recruiting portion comprises or consists of the sequence 5'-GUGG$N^c$AUAN$^a$UAUAACAAUAUgc-uaaAUGUUGUUAUAN$^b$UAUN$^d$CCAC-3' (SEQ ID NO: 25), where: $N^a$, $N^b$, $N^c$, and $N^d$ each may be a nucleotide A, G, C or U, provided that $N^a$ & $N^b$ form a mismatch basepair and $N^c$ & $N^d$ form a mismatch basepair upon stem loop formation; and whereby the gcuaa pentanucleotide forms a loop and the upstream and downstream sequences adjacent to gcuaa form a stem by base-pairing.

The recruiting portion may be linked at the 5' or 3' end to a targeting portion, optionally via a linker "L", that comprises one or more nucleotides, an oligopeptide or another chemical linker, such as polyethylene glycol (PEG).

Chemical Modification of the Oligonucleotides Constructs

Various chemistries and modification are known in the field of oligonucleotides that can be readily used in accordance with the invention. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. The ribose sugar may be modified by substitution of the 2'-O moiety with a lower alkyl (C1-4, such as 2'-O-Me), alkenyl (C2-4), alkynyl (C2-4), methoxyethyl (2'-MOE), or other substituent. Preferred substituents of the 2' OH group are a methyl, methoxyethyl or 3,3'-dimethylallyl group. The latter is known for its property to inhibit nuclease sensitivity due to its bulkiness, while improving efficiency of hybridization (Angus & Sproat FEBS 1993 Vol. 325, no. 1, 2, 123-7). Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art.

Length

The oligonucleotide constructs according to the invention may comprise between 20 and several hundred nucleotides. For practical reasons such as manufacturability and cost, the oligonucleotide constructs should preferably be shorter than 200 nucleotides. Preferably, the oligonucleotide constructs are between 20 and 100 nucleotides long, more preferably between 24 and 60 nucleotides, still more preferably between 30 and 50 nucleotides. The targeting portion of the oligonucleotide construct preferably comprises more than 10 nucleotides, preferably more than 11, 12, 13, 14, 15, 16 still more preferably more than 17 nucleotides. Longer targeting portions provide more specificity for the target site of the RNA sequence to be edited, less off-target effects due to unintentional (off-target) binding as well as more room to create secondary structures, such as stem-loop structures within the targeting portion itself, mismatches or wobble-bases (due to mismatches with one or more of the complementary base(s) in the targeted RNA sequence at or near the site to be edited), and so forth. Preferred targeting portions are complementary to the target RNA sequence over the entire length of the targeting portion except for the mismatch opposite the nucleotide to be edited, and optionally one or two wobble bases.

Conformation

It is known in the art, that RNA editing entities, such as hADARs, edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 can be increased to only convert particular adenosines by ensuring a mismatch in the dsRNA, by providing a targeting portion that comprises a mismatch opposite the adenosine to be edited. The mismatch is preferably created by providing a targeting portion having a cytidine or uridine, most preferably a cytidine, opposite the adenosine to be edited. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct according to the invention. After the mismatch has been resolved due to editing, the substrate is released and the oligonucleotide construct-editing entity complex is released from the target RNA sequence, which then becomes available for downstream biochemical processes, such as splicing and translation.

The desired level of specificity of editing the target RNA sequence may depend from application to application. Following the instructions in the present patent application, those of skill in the art will be capable of designing the targeting portion of the oligonucleotide construct according to their needs, and, with some trial and error, obtain the desired result.

The targeting portion of the oligonucleotide constructs of the invention will usually comprise the normal nucleotides A, G, U and C, but may also include inosine (I), for example instead of one or more G nucleotides. In a recruiting portion of an oligonucleotide construct according to the invention G may also be replaced by an I, although care must be taken that an I in the stem or the loop does not interfere with the formation of Z-DNA or Z-RNA conformations in those embodiments where this is desirable.

Editing Specificity

To prevent undesired editing of adenosines in the target RNA sequence in the region of overlap with the oligonucleotide construct, the targeting portion of the oligonucleotide construct may be chemically modified. It has been shown in the art, that 2'-O-methylation of the ribosyl-moiety of a nucleoside opposite an adenosine in the target RNA sequence dramatically reduces deamination of that adenosine by ADAR (Vogel et al. 2014 Angewandte Chemie Int. Ed. 53, 6267-71). Hence, by including 2'-methoxy (2'-OMe) nucleotides in desired position of the oligonucleotide construct, the specificity of editing may be dramatically improved. It is envisaged that other 2'-O substitutions of the ribosyl moiety, such as 2'-methoxyethyl (2'-MOE) and 2'-O-dimethylallyl groups may also reduce unwanted editing of the corresponding (opposite) adenosine in the target RNA sequence. Other chemical modifications are readily available to the person having ordinary skill in the art of oligonucleotide synthesis and design. The synthesis of such chemically modified oligonucleotide constructs and testing them in methods according to the invention does not pose an undue burden and other modifications are encompassed by the present invention.

Editing Entities

Editing entities will usually be proteinaceous in nature, such as the ADAR enzymes found in metazoans, including mammals. Editing entities may also comprise complexes of nucleic acid(s) and proteins or peptides, such as ribonucleoproteins. Editing enzymes may comprise or consist of nucleic acid(s) only, such as ribozymes. All such editing entities are encompassed by the present invention, as long as they are recruited by the oligonucleotide constructs according to the invention. Preferably, the editing entity is an enzyme, more preferably an adenosine deaminase or a cytidine deaminase, still more preferably an adenosine deaminase. When the editing entity is an adenosine deaminase, Y is preferably a cytidine or a uridine, most preferably a cytidine. The ones of most interest are the human ADARs, hADAR1 and hADAR2, including any isoforms thereof such as hADAR1 p110 and p150.

RNA editing enzymes known in the art, for which oligonucleotide constructs according to the invention may conveniently be designed, include the adenosine deaminases acting on RNA (ADARs), such as hADAR1 and hADAR2 in humans or human cells and cytidine deaminases. Human ADAR3 (hADAR3) has been described in the prior art, but reportedly has no deaminase activity.

It is known that hADAR1 exists in two isoforms; a long 150 kDa interferon inducible version and a shorter, 100 kDa version, that is produced through alternative splicing from a common pre-mRNA. Interestingly, only the longer isoform is capable of binding to the Z-DNA structure that can be comprised in the recruiting portion of the oligonucleotide construct according to the invention. Consequently, the level of the 150 kDa isoform present in the cell may be influenced by interferon, particularly interferon-gamma (IFN-gamma). hADAR1 is also inducible by TNF-alpha. This provides an opportunity to develop combination therapy, whereby interferon-gamma or TNF-alpha and oligonucleotide constructs comprising Z-DNA as recruiting portion according to the invention are administered to a patient either as a combination product, or as separate products, either simultaneously or subsequently, in any order. Certain disease conditions may already coincide with increased IFN-gamma or TNF-alpha levels in certain tissues of a patient, creating further opportunities to make editing more specific for diseased tissues.

Both the targeting portion and the recruiting portion may comprise or consist of nucleotides having chemical modifications that alter nuclease resistance, alter affinity of binding (expressed as melting temperature) or other properties. Examples of chemical modifications are modifications of the sugar moiety, including by cross-linking substituents within the sugar (ribose) moiety (e.g. as in LNA or locked nucleic acids), by substitution of the 2'-O atom with alkyl (e.g. 2'-O-methyl), alkynyl (2'-O-alkynyl), alkenyl (2'-O-alkenyl), alkoxyalkyl (e.g. methoxyethyl, 2'-MOE) groups, having a length as specified above, and the like. In addition, the phosphodiester group of the backbone may be modified by thioation, dithioation, amidation and the like to yield phosphorothioate, phosphorodithioate, phosphoramidate, etc., internucleosidic linkages. The internucleotidic linkages may be replaced in full or in part by peptidic linkages to yield in peptidonucleic acid sequences and the like. Alternatively, or in addition, the nucleobases may be modified by (de)amination, to yield inosine or 2'6'-diaminopurines and the like.

A further modification may be methylation of the C5 in the cytidine moiety of the nucleotide, to reduce potential immunogenic properties known to be associated with CpG sequences.

The architecture of the oligonucleotide constructs according to the invention may vary from "one legged" hairpins (FIG. 1 and FIG. 2), to "two legged" hairpins (FIG. 3), whereby the legs comprise the targeting portion or portions, and the body or core of the hairpin provides the recruiting portion (FIGS. 1-3). The leg or legs of the oligonucleotide construct will provide mismatching or wobbling nucleobases representing the opposite site of the editing site, e.g. an adenosine or cytidine to be edited, in the target RNA. For example, in case the oligonucleotide construct recruits ADAR activity, to edit an A to I conversion in the target RNA, the mismatch or wobble may comprise an adenosine, a guanine, an uridine or a cytidine residue, preferably a cytidine residue. Except for the mismatch or wobble opposite the editing site, the targeting portion will usually be perfectly complementary to the target RNA, although a limited number of imperfect matches, such as wobble or mismatching bases, may be allowable without unacceptably impairing the specificity and/or the strength of binding between the oligonucleotide construct and the target RNA sequence. The stem of the hairpin may consist of a perfectly complementary stretch of nucleotides, forming a double strand RNA structure over the entirety of its length. Alternatively, the stem of the hairpin may comprise one or more wobbling or non-matching opposing nucleotides, as long as the recognition of the oligonucleotide construct by the editing activity is not unacceptably impaired. It should be understood that the functioning of the editing activity in the cell at its natural editing sites may be reduced as a consequence of the recruitment of the entities responsible for the editing activity by the oligonucleotide constructs according to the invention. It will be understood by a person having ordinary skill in the art that the extent to which the editing entities inside the cell are redirected to other target sites may be regulated by varying the affinity of the recruiting portion of the oligonucleotide constructs according to the invention for the recognition domain of the editing entity. This may be done by reducing the affinity of the recruiting portion of the oligonucleotide construct for the editing entity through any one or combination of ways, including by changing the sequence of the stem, the size or structure (sequence, chemistry of the backbone, ribosyl, or nucleobase) of the loop or a combination of both. The exact modification may be determined through some trial and error and/or through computational methods based on structural interactions between the recruiting portion of the oligonucleotide construct and the recognition domain of the editing entity.

In addition, or alternatively, the degree of recruiting and redirecting the editing entity resident in the cell may be regulated by the dosing and the dosing regimen of the oligonucleotide construct. This is something to be determined by the experimenter (in vitro) or the clinician, usually in phase I and/or II clinical trials.

Preferably, the invention provides for the use of an oligonucleotide construct that consists of a single oligonucleotide (FIG. 1, FIG. 2 (panel A), FIG. 3) comprising both the targeting portion and the recruiting portion for editing nucleic acid sequences. However, an oligonucleotide construct comprising the use of two oligonucleotides (FIG. 2 (Panel B)), for example one comprising the targeting portion and one comprising the recruiting portion, is certainly within the ambit of the present invention. Hence, according to another embodiment the invention provides for two separate oligonucleotides, one comprising the targeting portion and the other comprising the recruiting portion, whereby the two oligonucleotides are designed in such a way that they have affinity towards each other, for example by antisense Watson-Crick base pairing between the two functional portions or of a sequence without a specific targeting or recruiting function, e.g. a linker sequence. Such a two component system may have advantages in terms of flexibility, adaptability (e.g. within the context of personalised medicine), manufacturability, cost of goods or otherwise. The two (or more) oligonucleotides in accordance with the multicomponent system, do not necessarily have to separate the different functions (targeting and recruiting) strictly. For example, the oligonucleotides may give rise to the targeting and a recruiting function only after assembling into a complex. In case the two oligonucleotides anneal, forming a dsRNA portion, they may actually create the recruiting function upon annealing. Annealing is one way of forming a complex, but it will be clear that there are other ways by which two (or more) oligonucleotide components may come together, thereby amalgamating the targeting and the recruiting function. Oligonucleotide constructs comprising more than two oligonucleotides are not excluded from the scope of the present invention, although larger the number of oligonucleotides per construct, the more complex the system in terms of manufacturing, analytics, formulation, administration or other aspects of handling, including logistics and costs.

The Mammalian Cell

The invention concerns the modification of target RNA sequences in eukaryotic, preferably metazoan, more preferably mammalian cells. In principle the invention can be used with cells from any mammalian species, but it is preferably used with a human cell.

The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject. Such cells include but are not limited to epithelial cells of the lung or the gastrointestinal tract, cells of the reproductive organs, muscle cells, cells of the eye, cells of the skin, cells from tissues and organs such as liver, kidney, pancreas, immune cells, cancerous cells, gland cells, brain cells, and the like.

The invention can also be used with mammalian cells which are not naturally present in an organism e.g. with a cell line or with an embryonic stem (ES) cell.

The invention can be used with various types of stem cell, including pluripotent stem cells, totipotent stem cells, embryonic stem cells, induced pluripotent stem cells, etc.

The cell can be located in vitro or in vivo. One advantage of the invention is that it can be used with cells in situ in a living organism, but it can also be used with cells in culture. In some embodiments cells are treated ex vivo and are then introduced into a living organism (e.g. re-introduced into an organism from whom they were originally derived).

The invention can also be used to edit target RNA sequences in cells within a so-called organoid. Organoids can be thought of as three-dimensional in vitro-derived tissues but are driven using specific conditions to generate individual, isolated tissues (e.g. see Lancaster & Knoblich, Science 2014, vol. 345 no. 6194 1247125). In a therapeutic setting they are useful because they can be derived in vitro from a patient's cells, and the organoids can then be re-introduced to the patient as autologous material which is less likely to be rejected than a normal transplant. Thus, according to another preferred embodiment, the invention may be practised on organoids grown from tissue samples taken from a patient (e.g. from their gastrointestinal tract; see Sala et al. J Surg Res. 2009; 156(2):205-12, and also Sato et al. Gastroenterology 2011; 141:1762-72); upon RNA editing in accordance with the invention, the organoids, or stem cells residing within the organoids, may be used to transplant back into the patient to ameliorate organ function.

The cell to be treated will generally have a genetic mutation. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations. Genes containing mutations of particular interest are discussed below. In some embodiments, however, the invention is used in the opposite way by introducing a disease-associated mutation into a cell line or an animal, in order to provide a useful research tool for the disease in question. As an example of creating a disease model, we have provided an oligonucleotide sequence that provides for the recruitment of editing activity in a human cell to create a mutation in the CEP290 gene, creating a cryptic splice site that forms the basis for a form of Leber's Congenital Amaurosis, the most common form of congenital child blindness.

A mutation to be reverted through RNA editing may have arisen on the level of the chromosome or some other form of DNA, such as mitochondrial DNA, or RNA, including pre-mRNA, ribosomal RNA or mitochondrial RNA. A change to be made may be in a target RNA of a pathogen, including fungi, yeasts, parasites, kinetoplastids, bacteria, phages, viruses etc, with which the cell or subject has been infected. Subsequently, the editing may take place on the RNA level on a target sequence inside such cell, subject or pathogen. Certain pathogens, such as viruses, release their nucleic acid, DNA or RNA into the cell of the infected host (cell). Other pathogens reside or circulate in the infected host. The oligonucleotide constructs of the invention may be used to edit target RNA sequences residing in a cell of the infected eukaryotic host, or to edit a RNA sequence inside the cell of a pathogen residing or circulating in the eukaryotic host, as long as the cells where the editing is to take place contain an editing entity compatible with the oligonucleotide construct administered thereto.

Without wishing to be bound by theory, the RNA editing through hADAR1 and hADAR2 is thought to take place on pre-mRNAs in the nucleus, during transcription or splicing. The RNA editing by cytidine deaminases is thought to take place on the mRNA level. Editing of mitochondrial RNA codons or non-coding sequences in mature mRNAs is not excluded.

The Target Sequence and the Change

The invention is used to make a change in a target RNA sequence in a eukaryotic cell through the use of an oligonucleotide construct that is capable of targeting a site to be edited and recruiting RNA editing entities resident in the cell to bring about the editing reaction(s). Preferred editing reactions are adenosine deaminations and cytidine deaminations, converting adenosines into inosines and cytidines into uridines, respectively. The changes may be in 5' or 3' untranslated regions of a target RNA, in (cryptic) splice sites, in exons (changing amino acids in protein translated from the target RNA, codon usage or splicing behaviour by changing exonic splicing silencers or enhancers, by introducing or removing start or stop codons), in introns (changing splicing by altering intronic splicing silencers or intronic splicing enhancers, branch points) and in general in any region affecting RNA stability, structure or functioning. The target RNA sequence may comprise a mutation that one may wish to correct or alter, such as a (a transition or a transversion). Alternatively, the target RNA sequence is deliberately mutated to create an altered phenotype (or genotype, in case of RNA based organisms, such as RNA viruses), where there was no mutation before. For example cell lines or animals may be made which carry changes (mutations) in a target RNA sequence, which may be used in assays or as (animal, organoid, etcetera) model systems to study disease, test experimental compounds against disease, and the like. The oligonucleotide constructs and methods according to the invention may be used in high throughput screening systems (in arrayed format) for making cell banks with a large variety of target RNAs, for example coding for a large variety of protein isoforms, for further experimentation, including compound screening, protein engineering and the like.

The target RNA may be any cellular or viral RNA sequence, but is more usually a pre-mRNA or a mRNA with a protein coding function.

Purely for ease of reference, and without the intention to limit the invention, the following table is provided to illustrate the potential codon changes that can be brought about by adenosine deaminase editing directed by oligonucleotides of the invention. The table particularly should not be interpreted as a limitation of the applicability of the invention to coding sequences in any RNA; as pointed out already, the invention can be practised on any RNA target comprising an adenosine, whether in a coding region, an intron, a non-coding exon (such as a 5'- or 3' untranslated region), in miRNAs, tRNAs, rRNAs and so on. To avoid any misunderstanding about the width of the applicability, changes that are inconsequential ('silent') from a coding perspective may still alter gene expression of a certain protein as some codons for the same amino acid may be more preferred than others and may lead, for instance, to different transcription stability or translation efficiency, causing the encoded protein to become more or less abundant than without the change.

| Target codon | Amino acid | Corrected codon | Amino acid |
|---|---|---|---|
| AAA | Lys | GAA | Glu |
|  |  | AGA | Arg |
|  |  | AAG | Lys |
|  |  | GGA | Gly |
|  |  | AGG | Arg |
|  |  | GAG | Glu |
|  |  | GGG | Gly |
| AAC | Asn | GAC | Asp |
|  |  | AGC | Ser |
|  |  | GGC | Gly |
| AAG | Lys | GAG | Glu |
|  |  | AGG | Arg |
|  |  | GGG | Gly |
| AAU | Arg | GAU | Asp |
|  |  | AGU | Ser |
|  |  | GGU | Gly |
| ACA | Thr | GCA | Ala |
|  |  | ACG | Thr |
|  |  | GCG | Ala |
| ACC | Thr | GCC | Ala |
| ACG | Thr | GCG | Ala |
| ACU | Thr | GCU | Ala |
| AGA | Arg | GGA | Gly |
|  |  | AGG | Arg |
|  |  | GGG | Gly |
| AGC | Ser | GGC | Gly |
| AGG | Arg | GGG | Gly |
| AGU | Ser | GGU | Gly |
| AUA | Ile | GAU | Asp |
|  |  | AUG | Met |
|  |  | GUG | Val |
| AUC | Ile | GUC | Val |
| AUG | Met | GUG | Val |
| AUU | Ile | GUU | Val |
| CAA | Gln | CGA | Arg |
|  |  | CAG | Gln |
|  |  | CGG | Arg |
| CAC | His | CGC | Arg |
| CAG | Gln | CGG | Arg |
| CAU | His | CGU | Arg |
| CCA | Pro | CCG | Pro |
| CGA | Arg | CGG | Arg |
| CUA | Leu | CUG | Leu |
| GAA | Glu | GGA | Gly |
|  |  | GAG | Glu |
|  |  | GGG | Gly |
| GCA | Ala | GCG | Ala |
| GUA | Val | GUG | Val |
| GGA | Gly | GGG | Gly |
| GAC | Asp | GGC | Gly |
| GAG | Glu | GGG | Gly |
| GAU | Asp | GGU | Gly |
| UAA | Stop | UGA | Stop |
|  |  | UAG | Stop |
|  |  | UGG | Trp |
| UCA | Ser | UCG | Ser |
| UGA | Stop | UGG | Trp |
| UUA | Leu | UUG | Leu |
| UAC | Tyr | UGC | Cys |
| UAG | Stop | UGG | Trp |
| UAU | Tyr | UGU | Cys |

Particularly interesting target adenosines for editing using oligonucleotides according to the invention are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, protein cleavage by proteases (to mature the protein and/or as part of the intracellular routing), and so forth.

A host of genetic diseases are caused by G to A mutations, and these are preferred target diseases because adenosine deamination at the mutated target adenosine will reverse the mutation to wild-type. However, reversal to wild-type may not always be necessary to obtain a beneficial effect. Modification of an A to G in a target may also be beneficial if the wild-type nucleotide is other than a G. In certain circumstances this may be predicted to be the case, in others this may require some testing. In certain circumstances, the modification from an A in a target RNA to G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A to G transition brought about by editing in accordance with the invention is in a non-coding RNA, or a non-coding part of an RNA, the consequence may also be inconsequential or less severe than the original mutation. Those of ordinary skill in the art will understand that the applicability of the current invention is very wide and is not even limited to preventing or treating disease. The invention may also be used to modify transcripts to study the effect thereof, even if, or particularly when, such modification induces a diseased state, for example in a cell or a non-human animal model.

Preferred examples of genetic diseases that can be prevented and/or treated with oligonucleotides according to the invention are any disease where the modification of one or more adenosines in a target RNA will bring about a (potentially) beneficial change.

Transcribed RNA sequences that are potential target RNA sequences according to the invention, containing mutations of particular interest include, but are not limited to those transcribed from the CFTR gene (the cystic fibrosis transmembrane conductance regulator), dystrophin, huntingtin, neurofibromin 1, neurofibromin 2, the β-globin chain of haemoglobin, CEP290 (centrosomal protein 290 kDa), the HEXA gene of the β-hexosaminidase A, and any one of the Usher genes (e.g. USH2B encoding Usherin) responsible for a form of genetic blindness called Usher syndrome. A more extensive list is presented further below. The target sequence will be selected accordingly, and the oligonucleotide construct will include the desired modification in order to correct the mutation.

Those skilled in the art of CF mutations recognise that between 1000 and 2000 mutations are known in the CFTR gene, including R117H, G542X, G551D, R553X, W1282X, and N1303K.

In general, mutations in any target RNA that can be reversed using oligonucleotide constructs according to the invention are G to A mutations, in the case of adenosine deaminase recruitment, and U to C mutations in the case of cytidine deaminase recruitment, and oligonucleotide constructs can be designed accordingly. Mutations that may be targeted using oligonucleotide constructs according to the invention also include C to A, U to A (T to A on the DNA level) in the case of recruiting adenosine deaminases, and A to C and G to C mutations in the case of recruiting cytidine deaminases. Although RNA editing in the latter circumstances may not necessarily revert the mutation to wild-type, the edited nucleotide may give rise to an improvement over the original mutation. For example, a mutation that causes an in frame stop codon—giving rise to a truncated protein, upon translation—may be changed into a codon coding for an amino acid that may not be the original amino acid in that position, but that gives rise to a (full length) protein with at least some functionality, at least more functionality than the truncated protein.

The target sequence is endogenous to the eukaryotic, preferably mammalian, more preferably human cell. Thus the target sequence is not, for instance, a transgene or a marker gene which has been artificially introduced at some point in the cell's history, but rather is a gene that is naturally present in the cell (whether in mutant or non-mutant form).

The invention is not limited to correcting mutations, as it may instead be useful to change a wild-type sequence into a mutated sequence by applying oligonucleotides according to the invention. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding, or is involved in secondary structure defining the stability of the mRNA. As noted above, therefore, the invention can be used to provide research tools for diseases, to introduce new mutations which are less deleterious than an existing mutation, etc.

Applications of the Oligonucleotide Constructs

The amount of oligonucleotide constructs to be administered, the dosage and the dosing regime can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of oligonucleotide could compete for binding to a nucleic acid editing entity (e.g. ADAR) within a cell, thereby depleting the amount of the entity which is free to take part in RNA editing, but routine dosing trials will reveal any such effects for a given oligonucleotide and a given target.

One suitable trial technique involves delivering the oligonucleotide construct to cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples.

A method of the invention can thus include a step of identifying the presence of the desired change in the cell's target RNA sequence, thereby verifying that the target RNA sequence has been modified. This step will typically involve sequencing of the relevant part of the target RNA, or a cDNA copy thereof (or a cDNA copy of a splicing product thereof, in case the target RNA is a pre-mRNA), as discussed above, and the sequence change can thus be easily verified. Alternatively the change may be assessed on the level of the protein (length, glycosylation, function or the like), or by some functional read-out, such as a(n) (inducible) current, when the protein encoded by the target RNA sequence is an ion channel, for example. In the case of CFTR function, an Ussing chamber assay or an NPD test in a mammal, including humans, are well known to a person skilled in the art to assess restoration or gain of function.

After RNA editing has occurred in a cell, the modified RNA can become diluted over time, for example due to cell division, limited half-life of the edited RNAs, etc. Thus, in practical therapeutic terms a method of the invention may involve repeated delivery of an oligonucleotide construct until enough target RNAs have been modified to provide a tangible benefit to the patient and/or to maintain the benefits over time.

Delivery of the Oligonucleotide Construct

Oligonucleotide constructs of the invention are particularly suitable for therapeutic use, and so the invention provides a pharmaceutical composition comprising an oligonucleotide construct of the invention and a pharmaceutically acceptable carrier. In some embodiments of the invention the pharmaceutically acceptable carrier can simply be a saline solution. This can usefully be isotonic or hypotonic, particularly for pulmonary delivery.

The invention also provides a delivery device (e.g. syringe, inhaler, nebuliser) which includes a pharmaceutical composition of the invention.

The invention also provides an oligonucleotide construct of the invention for use in a method for making a change in a target RNA sequence in a mammalian, preferably human cell, as described herein. Similarly, the invention provides the use of an oligonucleotide construct of the invention in the manufacture of a medicament for making a change in a target RNA sequence in a mammalian, preferably human cell, as described herein.

Formulation, Dosing and Mode of Administration for Use in Therapy

The oligonucleotide constructs according to the invention are suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by inhalation (e.g. through nebulization), intranasally, orally, by injection or infusion, intravenously, subcutaneously, intradermally, intra-cranially, intramuscularly, intra-tracheally, intra-peritoneally, intra-rectally, by direct injection into a tumor, and the like. Administration may be in solid form, in the form of a powder, a pill, or in any other form compatible with pharmaceutical use in humans.

The invention is particularly suitable for treating genetic diseases, such as cystic fibrosis, albinism, alpha-1-antitrypsin deficiency, Alzheimer disease, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermolysis bullosa, Fabry disease, Factor V Leiden associated disorders, Familial Adenomatous Polyposis, Galactosemia, Gaucher's Disease, Glucose-6-phosphate dehydrogenase deficiency, Haemophilia, Hereditary Hemochromatosis, Hunter Syndrome, Huntington's disease, Hurler Syndrome, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Parkinson's disease, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, various forms of cancer (e.g. BRCA1 and 2 linked breast cancer and ovarian cancer), and the like.

In some embodiments the oligonucleotide construct can be delivered systemically, but it is more typical to deliver an oligonucleotide construct to cells in which the target sequence's phenotype is seen. For instance, mutations in CFTR cause cystic fibrosis which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI EFLOW®(RAPID) or the I-NEB® from Respironics. The inventors have found that inhaled use of oligonucleotide constructs can lead to systemic distribution of the oligonucleotide construct and uptake by cells in the gut, liver, pancreas, kidney and salivary gland tissues, among others. It is therefore to be expected that inhaled delivery of oligonucleotide constructs according to the invention can also target these cells efficiently, which in the case of CFTR gene targeting could lead to amelioration of gastrointestinal symptoms also associated with cystic fibrosis. For other target sequences, depending on the disease and/or the target organ, administration may be topical (e.g. on the skin), intradermal, subcutaneous, intramuscular, intravenous, oral, ocular injection, etc.

In some diseases the mucus layer shows an increased thickness, leading to a decreased absorption of medicines via the lung. One such a disease is chronical bronchitis, another example is cystic fibrosis. Various forms of mucus normalizers are available, such as DNAses, hypertonic saline or mannitol, which is commercially available under the name of BRONCHITOL®. When mucus normalizers are used in combination with RNA editing oligonucleotide constructs, such as the oligonucleotide constructs according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the oligonucleotide constructs according to the invention can be combined with administration of small molecule for treatment of CF, such as potentiator compounds for example KALYDECO® (ivacaftor; VX-770), or corrector compounds, for example VX-809 (lumacaftor) and/or VX-661. Other combination therapies in CF may comprise the use of an oligonucleotide construct according to the invention in combination with an inducer of adenosine deaminase, using IFN-gamma or TNF-alpha.

Alternatively, or in combination with the mucus normalizers, delivery in mucus penetrating particles or nanoparticles can be applied for efficient delivery of RNA editing molecules to epithelial cells of for example lung and intestine. Accordingly, administration of an oligonucleotide construct according to the invention to a subject, preferably a human subject, preferably uses delivery in mucus penetrating particles or nanoparticles.

Chronic and acute lung infections are often present in patients with diseases such as cystic fibrosis. Antibiotic treatments reduce bacterial infections and the symptoms of those such as mucus thickening and/or biofilm formation. The use of antibiotics in combination with oligonucleotide constructs according to the invention could increase effectiveness of the RNA editing due to easier access of the target cells for the oligonucleotide construct. Accordingly, administration of an oligonucleotide construct according to the invention to a subject, preferably a human subject, is preferably combined with antibiotic treatment to reduce bacterial infections and the symptoms of those such as mucus thickening and/or biofilm formation. The antibiotics can be administered systemically or locally or both.

For application in for example cystic fibrosis patients the oligonucleotide constructs according to the invention, or packaged or complexed oligonucleotide constructs according to the invention may be combined with any mucus normalizer such as a DNase, mannitol, hypertonic saline and/or antibiotics and/or a small molecule for treatment of CF, such as potentiator compounds for example ivacaftor, or corrector compounds, for example lumacaftor and/or VX-661.

To increase access to the target cells, Broncheo-Alveolar Lavage (BAL) could be applied to clean the lungs before administration of the oligonucleotide constructs according to the invention.

The invention also provides an oligonucleotide construct comprising the nucleotide sequence of any one of SEQ ID NOs: 1 to 3:

```
GFP
                                            SEQ ID NO: 1
5'-cgcgcgttttcgcgcgGCUGAAC*CACUGCAC- 3'

CEP290
                                            SEQ ID NO: 2
5'-cgcgcgttttcgcgcgGAGAUAC*UCACAAUU-3'

CFTR
                                            SEQ ID NO: 3
5'-cgcgcgttttcgcgcgCGUUGAC*CUCCACUC-3'
```

Corresponding sequence SEQ ID NO: 9 G551D mRNA
3T-GCAACUA*GAGGUGAG-5'
small letters=DNA with propensity to form Z-DNA structure
Bold underlined=2'-O-methyl
Italics=Phosphorothioate internucleosidic linkages and 2'-O-methyl
C*=base opposite the target adenosine to be edited Similarly, the invention also provides an oligonucleotide construct comprising the nucleotide sequence of any one of SEQ ID NOs: 16 to 22 (and optionally the nucleic modifications described in Example 1 for such nucleotide sequences) or any one of SEQ ID NOs: 2, 3, 28, 38, 39, 40 and 41 (and optionally the nucleic modifications described in Examples 2-5 for such nucleotide sequences).

General

The terms "adenine", "guanine", "cytosine", "thymine", "uracil" and hypoxanthine (the nucleobase in inosine) refer to the nucleobases as such.

The terms adenosine, guanosine, cytidine, thymidine, uridine and inosine, refer to the nucleobases linked to the (desoxy)ribosyl sugar.

The term "nucleoside" refers to the nucleobase linked to the (deoxy)ribosyl sugar.

The term nucleotide refers to the respective nucleobase-(deoxy)ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like.

Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide.

Sometimes the terms nucleobase, nucleoside and nucleotide are used interchangeably, unless the context clearly requires differently.

Whenever reference is made to an "oligonucleotide", both oligoribonucleotides and desoxyoligoribonucleotides are meant unless the context dictates otherwise. Whenever reference is made to an oligoribonucleotide it may comprise the bases A, G, C, U or I. Whenever reference is made to a desoxyoligoribonucleotide it may comprise the bases A, G, C, T or I.

Whenever reference is made to nucleotides in the oligonucleotide construct, such as cytosine, 5-methylcytosine, 5-hydroxymethylcytosine and β-D-Glucosyl-5-hydroxymethylcytosine are included; when reference is made to adenine, N6-Methyladenine and 7-methyladenine are included; when reference is made to uracil, dihydrouracil, 4-thiouracil and 5-hydroxymethyluracil are included; when reference is made to guanine, 1-methylguanine is included.

Whenever reference is made to nucleosides or nucleotides, ribofuranose derivatives, such as 2'-desoxy, 2'-hydroxy, and 2'-O-substituted variants, such as 2'-O-methyl, are included, as well as other modifications, including 2'-4' bridged variants.

Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term "comprising" encompasses "including" as well as "consisting" e.g. a composition "comprising" X may consist exclusively of X or may include something additional e.g. X+Y.

The term "about" in relation to a numerical value x is optional and means e.g. x±10%.

The word "substantially" does not exclude "completely" e.g. a composition which is "substantially free" from Y may be completely free from Y. Where relevant, the word "substantially" may be omitted from the definition of the invention.

The term "downstream" in relation to a nucleic acid sequence means further along the sequence in the 3' direction; the term "upstream" means the converse. Thus in any sequence encoding a polypeptide, the start codon is upstream of the stop codon in the sense strand, but is downstream of the stop codon in the antisense strand.

References to "hybridisation" typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity.

BRIEF DESCRIPTION OF THE DRAWINGS

FIGS. 4a and 4b differ only by contrast.

Figure 1:
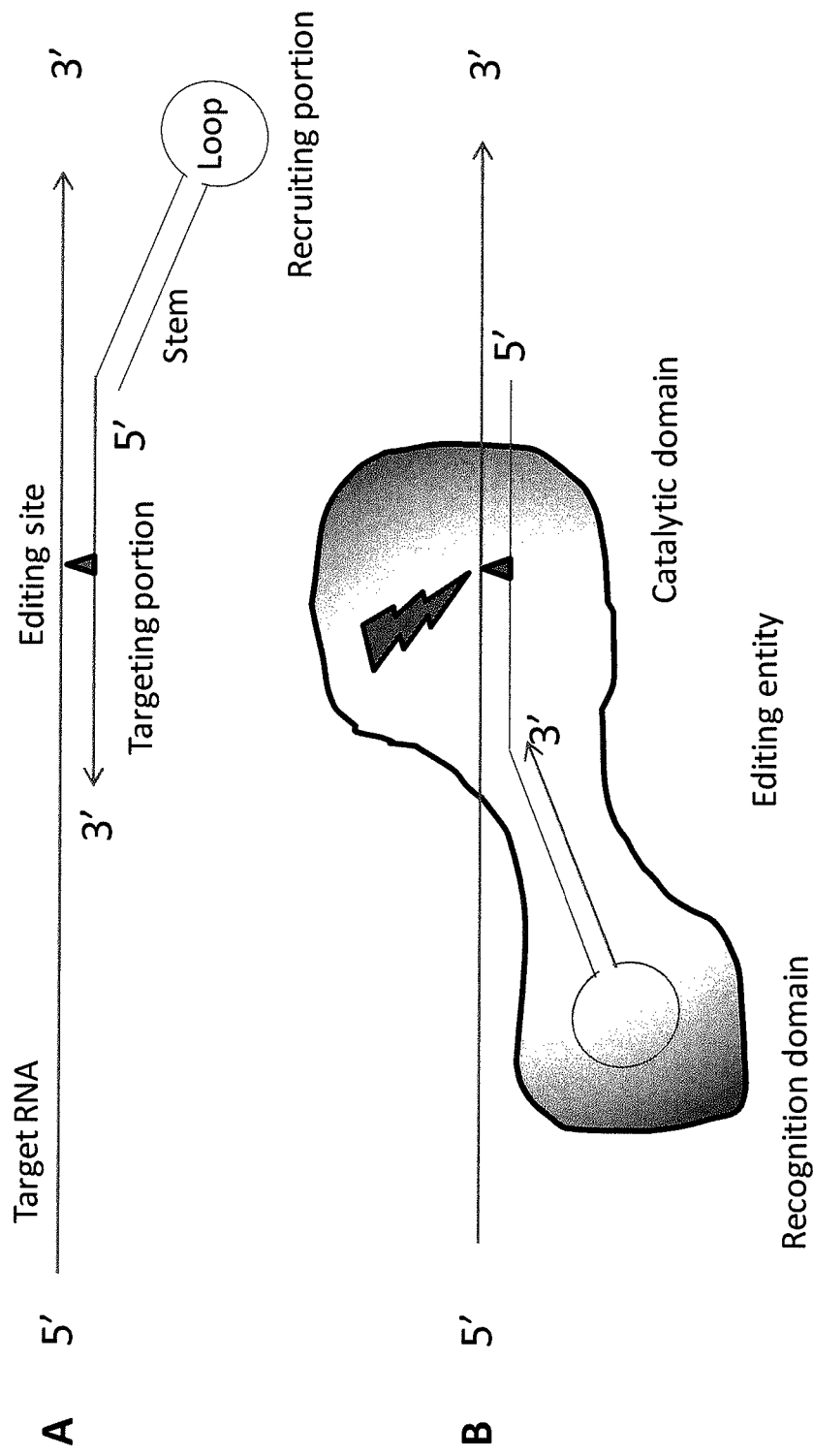
FIG. 1: Cartoon of a target RNA sequence and an oligonucleotide construct according to the invention; panel A: the oligonucleotide construct is designed as a single oligonucleotide "one-legged" construct, with the targeting portion at its 3' end and the recruiting portion at its 5' end. Panel B: the oligonucleotide construct is designed as a single oligonucleotide "one-legged" construct, with the targeting portion at its 5' end and the recruiting portion at its 3'end; the editing entity is depicted as a grey structure, depicting the recognition domain on the left-hand side and the catalytic domain on the right-hand side, indicating the deamination reaction (flash) at the target site.
Figure 2:
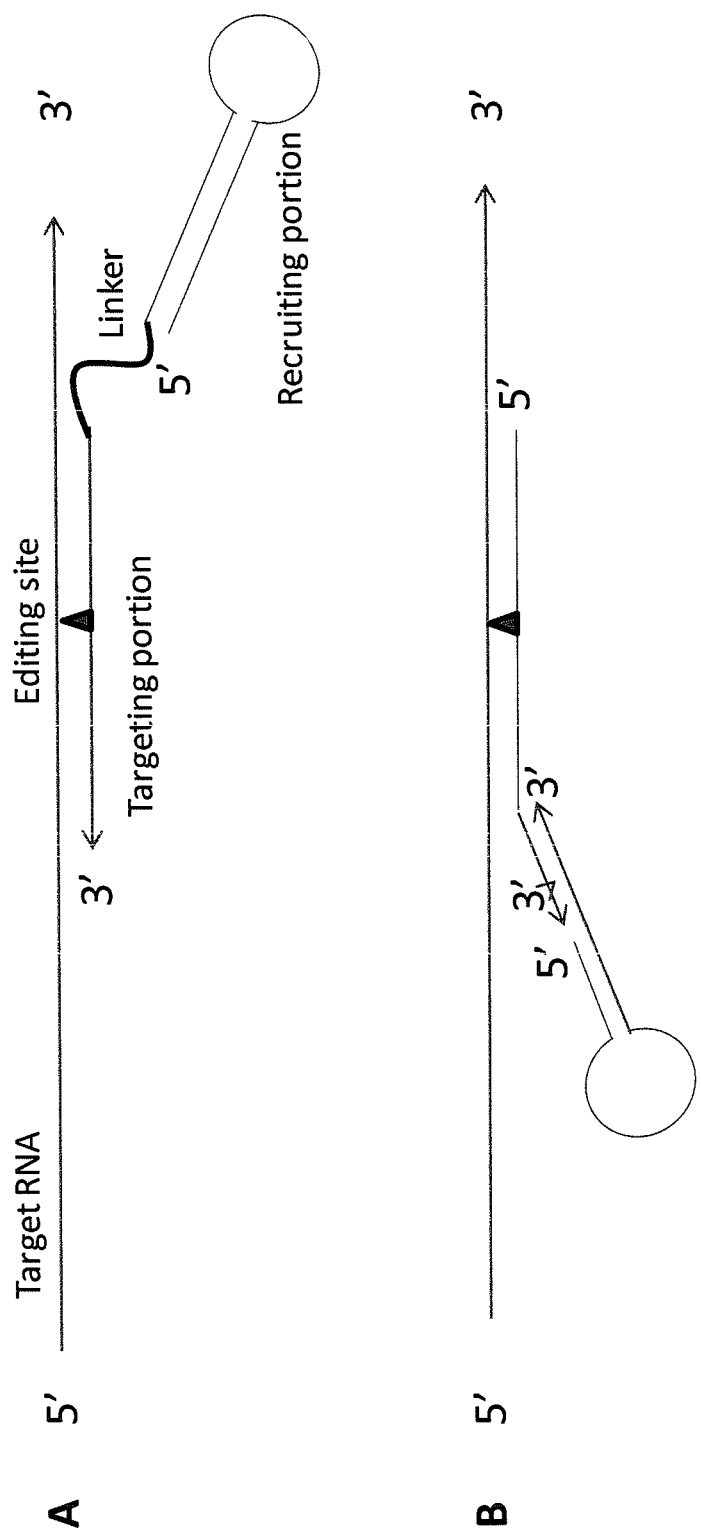
FIG. 2: Cartoon of the target RNA structure with oligonucleotide construct: panel A shows the oligonucleotide construct with a Linker between the targeting portion and the recruiting portion; panel B shows the embodiment where the oligonucleotide construct comprises two oligonucleotide sequences—not covalently bound—interacting through Watson-Crick antisense base pairing by their respective 3' segments.
Figure 3:
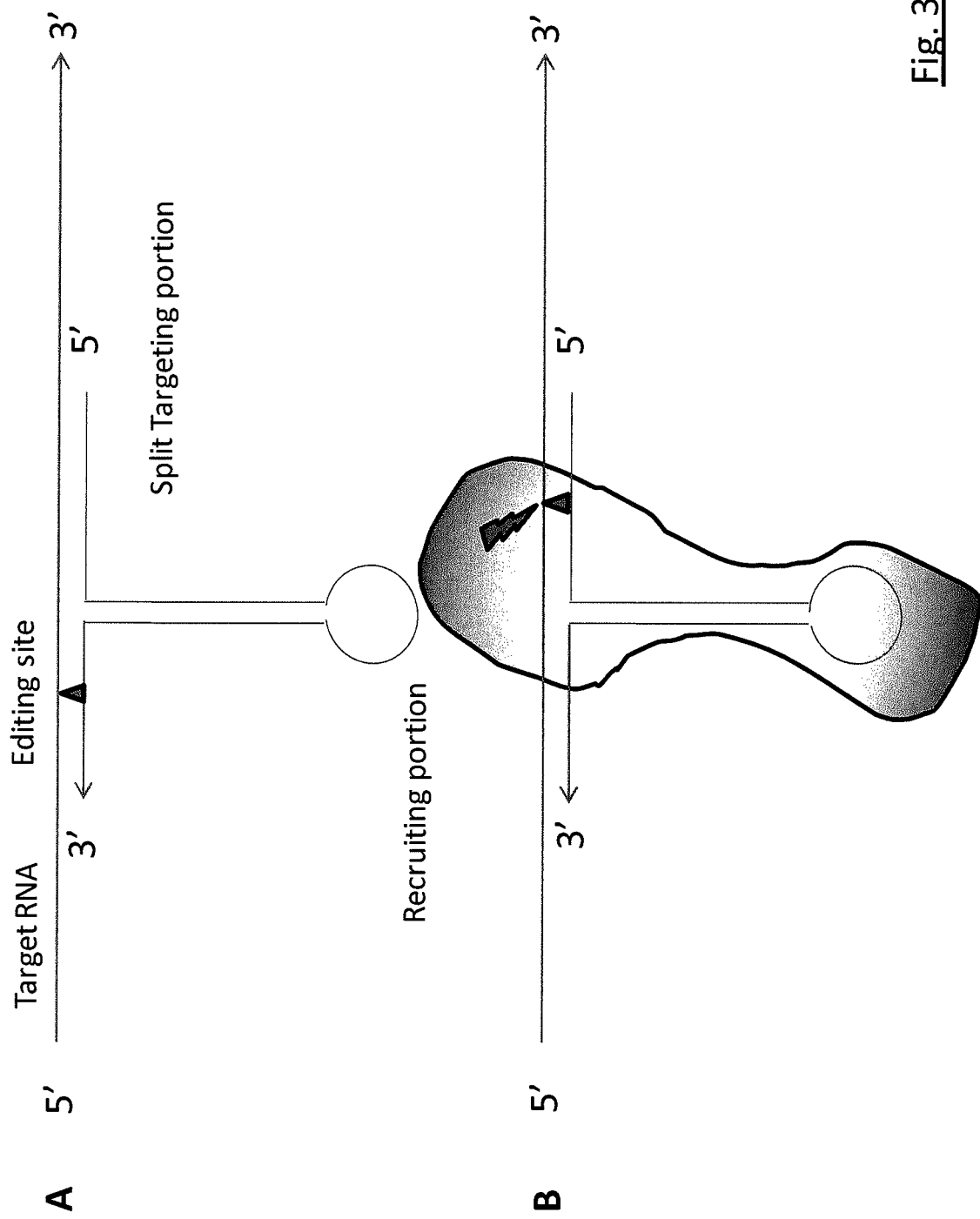
FIG. 3: Cartoon of the target RNA structure with the oligonucleotide construct in its "two-legged" format, where the targeting portion is separated (or "split") by the recruiting portion; panel A shows the editing site upstream in the target RNA sequence, relative to the recruiting portion of the oligonucleotide construct; panel B shows the editing site downstream in the targeting RNA sequence, relative to the recruiting portion of the oligonucleotide construct.

All embodiments illustrated in the drawings may be combined, as explained in the detailed description of the invention herein.

MODES FOR CARRYING OUT THE INVENTION

Example 1: Reversing a Non-Sense Mutation in a GFP Target RNA by Site-Directed a to I Editing Oligonucleotide construct to be used: 5'-cgcgcgttttcgcgcg GCUGAAC*CACUGCAC-3' (SEQ ID NO: 1). HeLa cells (ATCC, CCL-2) are cultured in Dulbecco's modified Eagle's medium (Life Technologies) supplemented with 10% heat-inactivated fetal bovine serum. Cells are kept in an atmosphere of humidified air with 5% $CO_2$. The cells are seeded in 24-well plate one day before the transfection and when they reach be 70-80% confluency. The GFP reporter construct with an abolished GFP activity because of a stop codon TGA was used. 100-200 ng of plasmid DNA and 500 ng oligonucleotide (10-100 pmol) construct are mixed in the appropriate amount of Opti-MEM I Medium (Life Technologies) and Lipofectamine 2000 reagent and the cells are transfected according to the manufacturer's procedure. The cells are incubated at 37° C. in a $CO_2$ incubator and the medium is replaced after 4-6 hours. After 48 hours the cells are analyzed under the fluorescent microscope to assess the efficiency of the oligo to restore GFP expression.

Further experiments again used a mutant GFP having an internal TAG stop codon due to a G→A point mutation, expressed from a plasmid ('pGFPstop57'). The cells were additionally transfected with a plasmid encoding ADAR2 to ensure that the cells were able to perform RNA editing. Various oligonucleotides were prepared for restoring GFP expression via deamination of the mutant A residue, based on the principle of a targeting portion specific for the GFP mutation and a recruiting portion based on GluR-B.

Seven RNA oligonucleotides were tested, and these targeted short, medium or long forms of GluR-B (S/M/L; different lengths of the recruiting portion). In addition, these had the targeting and recruiting portions in either order (upstream/downstream), and in some cases the oligos included chemically modified regions (the recruiting portion was chemically modified to include 2'-OMe sugars and phosphorothioate linkages; the targeting portion was modified in the same way, except for the mutant A position (double underlined) and its two flanking nucleotides). All oligos include SEQ ID NO: 7 (underlined), and GFP targeting portions are in bold text:

mean values of GFP mean fluorescent intensity (MFI) are calculated. Overlay histograms are created using the layout editor.

Figure 4A:
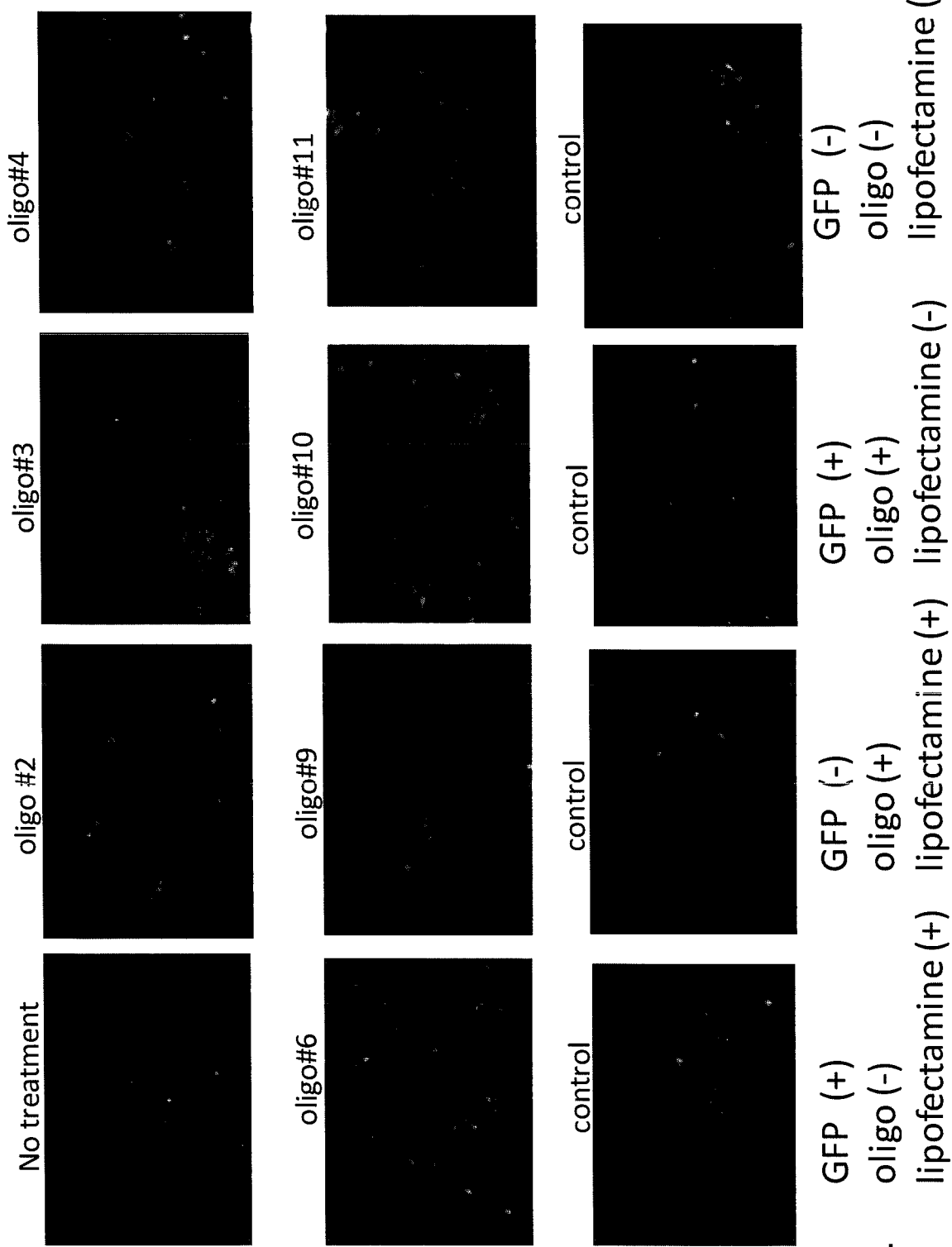
FIGS. 4a and 4b: Fluorescence microscopy of wells showing green fluorescence in HeLa cells after lipofectamine transfection with pGFPstop57 and the indicated oligonucleotides, except: the top-left panel is untreated cells; the bottom four panels are controls which did not receive at least one of the indicated components.
Figure 4B:
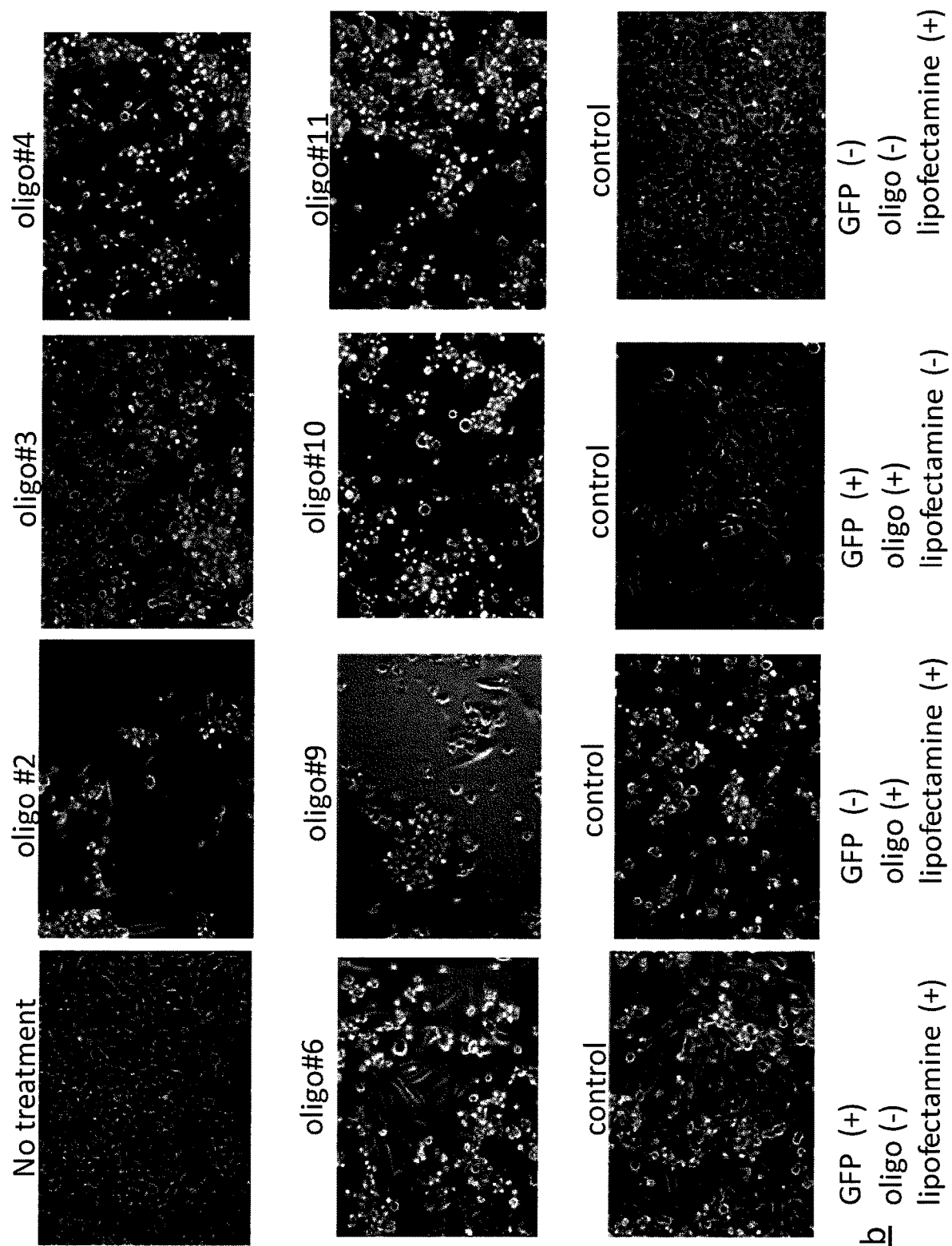

Results for cells transfected without the ADAR plasmid are shown in FIGS. 4a and 4B, and green fluorescence above the levels seen in controls (which is due to autofluorescence of cells and/or medium components) is clearly visible for all seven oligos. Oligos #10 & #11 gave the best results (both having a long GluR-B recruiting portion), and the oligo with an upstream recruiting portion (#11) was slightly better.

Figure 5:
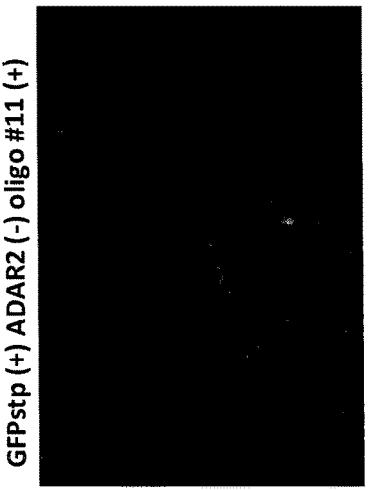
FIG. 5: Fluorescence microscopy of wells showing green fluorescence in HeLa cells after lipofectamine transfection with pGFPstop57, pADAR2, and oligonucleotide #11 at various ratios of the two plasmids. The top-left panel is untreated cells; the bottom panels shows cells with a plasmid encoding non-mutant GFP rather than pGFPstop57.
Figure 5:
Figure 5:
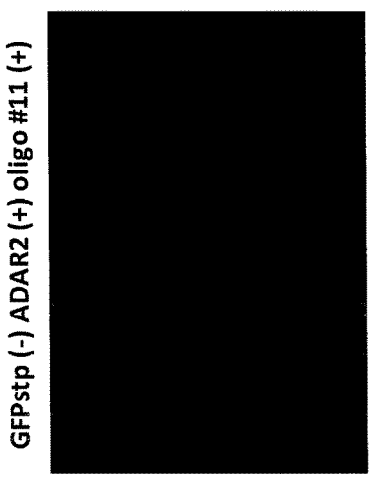
Figure 5:
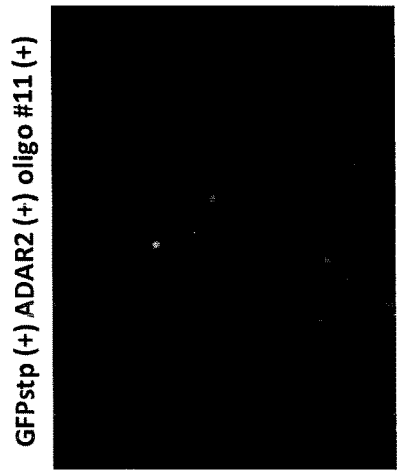
Figure 5:
Figure 5:
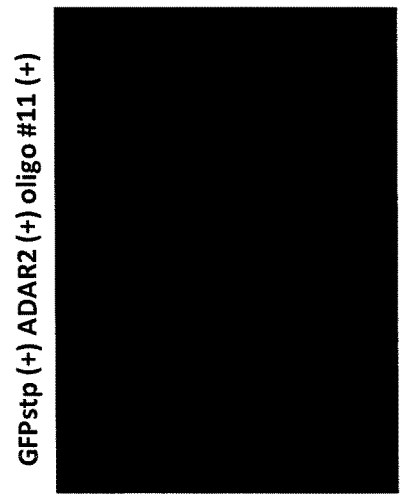
Figure 5:
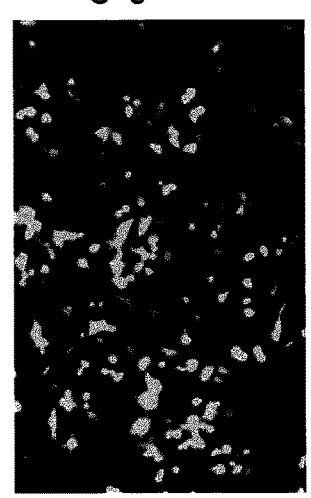

Oligo #11 was therefore chosen for further studies in combination with the ADAR2-encoding plasmid. FIG. 5 again shows that cells treated with oligo #11 fluoresce above levels seen in negative controls. For comparison, cells were transfected with a plasmid encoding a non-mutant GFP and the expected fluorescence was seen (FIG. 5, bottom panel).

Figure 6:
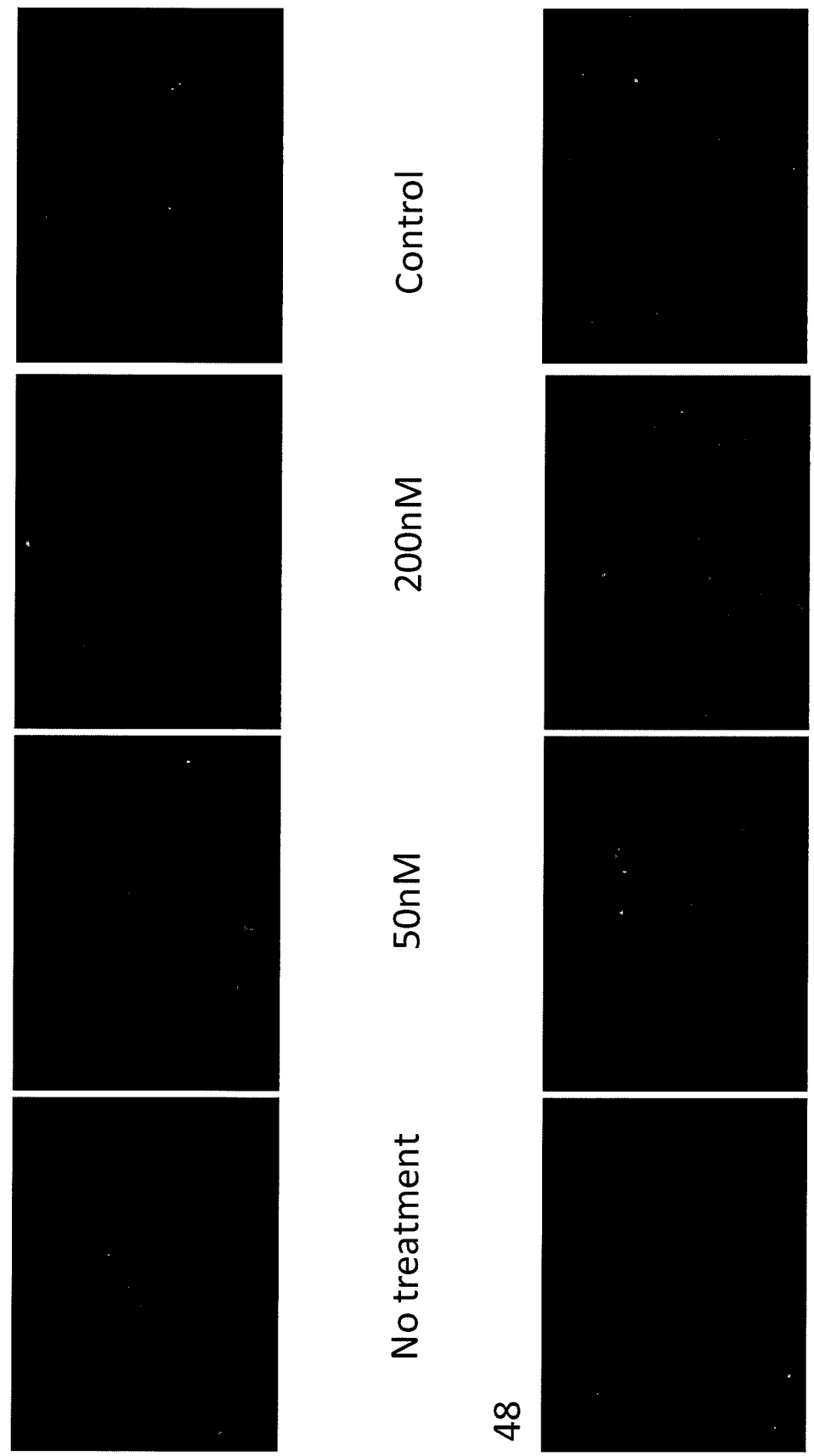
FIG. 6: Fluorescence microscopy of wells showing green fluorescence in HeLa cells 24 or 48 hours after no treatment, or transfection with 50 nM or 200 nM oligonucleotide #11 (or with 500 nM of a control oligonucleotide) together with pGFPstop57.

Different concentrations of oligo #11 were tested, ranging from 50-1500 nM. FIG. 6 shows example results after 24 or 48 hours using 50 and 200 nM, along with untreated cells (left) and control cells which were tested with 500 nM of a control oligo having the same length and chemical modifications as oligo #11. Oligo #11 showed a time-dependent increase in fluorescence, which was not seen with the control oligo.

Figure 7:
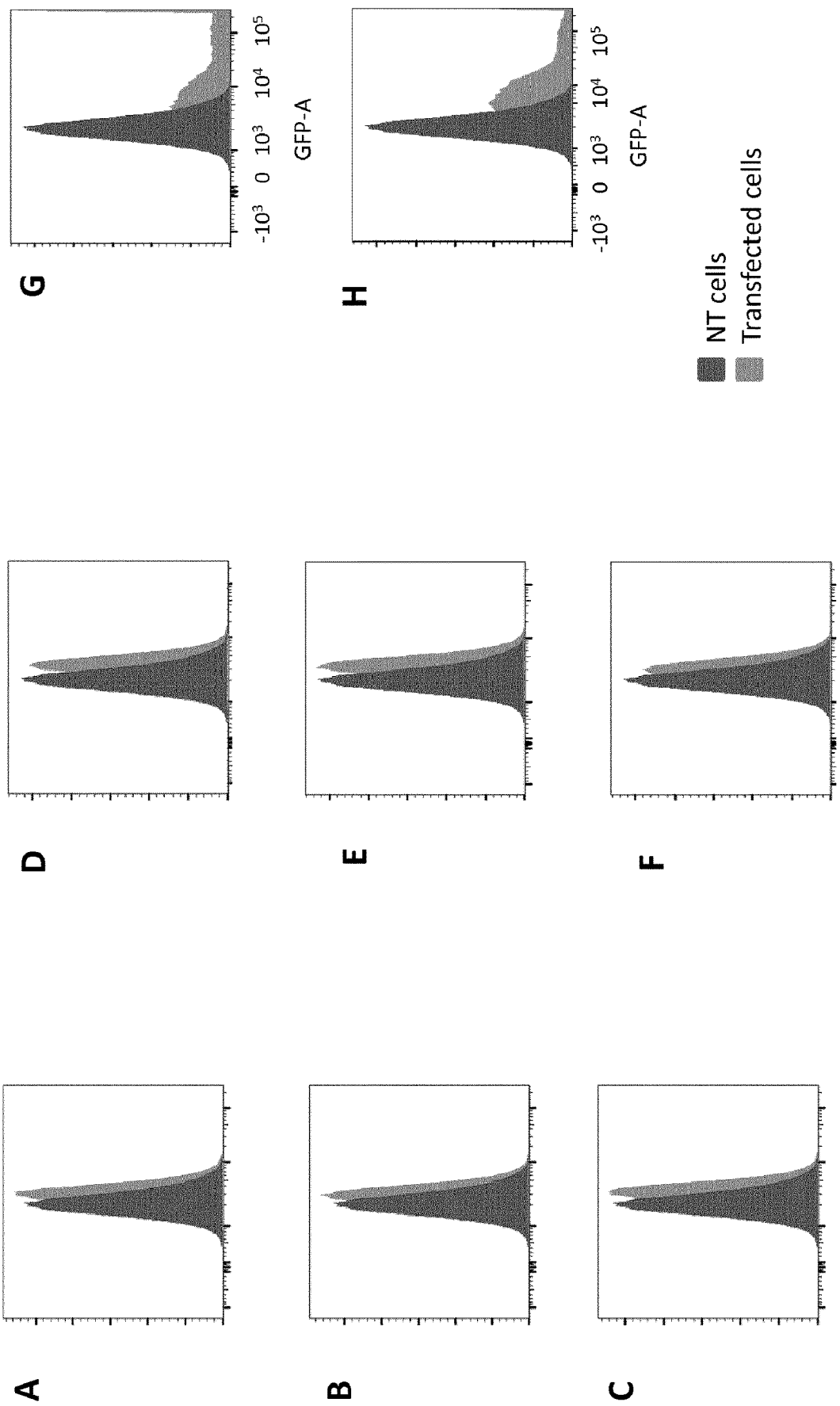
FIG. 7: FACS spectra of non-treated (left peak) or transfected (right peak) HeLa cells. In panels A-F cells were transfected with pGFPstop57 and oligonucleotide #11. In panels B-F (but not panel A) cells were also transfected with pADAR2. In panels F and H non-mutant GFP was expressed.

The oligonucleotide's effect on GFP expression was also visible by FACS (FIG. 7). Cells treated with oligo #11, with

| Oligo | GluR-B (length & position) | Modification | Sequences (SEQ ID NO:) |
|---|---|---|---|
| #2 | S | 3' | unmodified | GUGUUGGCCAUGGAACAUAUAACAAUAUgcuaaAUGUUGUUAUA (SEQ ID NO: 16) |
| #3 | S | 5' | 2'OMe-PS | UAUAACAAUAUgcuaaAUGUUGUUAUAGUGUUGGCCAUGGAACA (SEQ ID NO: 17) |
| #4 | S | 3' | 2'OMe-PS | GUGUUGGCCAUGGAACAUAUAACAAUAUgcuaaAUGUUGUUAUA (SEQ ID NO: 18) |
| #6 | M | 3' | unmodified | GUGUUGGCCAUGGAACAAUAGUAUAACAAUAUgcuaaAUGUUGUUAUAGUAU (SEQ ID NO: 19) |
| #9 | L | 5' | unmodified | GGAAUAGUAUAACAAUAUgcuaaAUGUUGUUAUAGUAUCCCGUGUUGGCCAUGGAACA (SEQ ID NO: 20) |
| #10 | L | 3' | unmodified | GUGUUGGCCAUGGAACAGGAAUAGUAUAACAAUAUgcuaaAUGUUGUUAUAGUAUCCC (SEQ ID NO: 21) |
| #11 | L | 5' | 2'OMe-PS | GGAAUAGUAUAACAAUAUgcuaaAUGUUGUUAUAGUAUCCCGUGUUGGCCAUGGAACA (SEQ ID NO: 22) |

HeLa cells are cultured in Dulbecco's modified Eagle's medium supplemented with 10% heat-inactivated fetal bovine serum. Cells are kept in an atmosphere of humidified air with 5% $CO_2$. $8 \times 10^4$ cells are seeded in one well of a 24-well plate one day before transfection and when they reach 70-80% confluency are transiently transfected with (i) oligonucleotide+GFPstop57 plasmid or (ii) oligonucleotide+GFPstop57+ADAR2 plasmids by using Lipocetamine 2000 according to the manufacturer's procedure. The medium is refreshed 24 hours after the transfection, and GFP expression is checked under the fluorescent microscope 24 hours later.

FACS analysis is also performed. The cells are trypsinized and collected in an Eppendorf tube and then resuspended in Flow Cytometry Staining Buffer. Intact cells are selected based on morphological properties using forward scatter and side scatter, excluding debris. Of the intact cells, median and (panels B-F) or without (panel A) the ADAR2 plasmid, displayed an increase in GFP fluorescence relative to untreated cells (left-hand peak). Non-mutant GFP was used as a positive control (panels G-H).

Example 2: Introducing a Cryptic Splice Site in a CEP290 Target RNA by Site-Directed A to I Editing Oligonucleotide construct to be used: 5'-cgcgcgttttcgcgcg GAGAUAC*UCACAAUU-3' (SEQ ID NO: 2)

All cell lines are human fibroblasts, generated from skin biopsies. FBL1 (CL10-00008) and FBL2 (CL12-00027) are wild type and represent control cell lines, FBL3 (CL12-00035) and FBL4 (CL12-00036) are both homozygous mutant for a mutation in CEP290 (c.2991+1655A>G). All cell lines are grown in DMEM medium (Life Technologies) supplemented with 20% FBS, 1% Pen/strep and 1% sodium pyruvate.

A day before transfection, cells are seeded in a density of 2×10⁵/well on a 6-well plate in a total volume of 2.5 ml of medium. The day of the transfection, the AON to be tested is added to each well in a final concentration of 100 nM using maxPEI (Poliscience) as a transfection agent, with a mass ratio oligo:PEI of 1:4. After 24 h, cells are washed with PBS and cell lysate is collected and frozen at −80° C.

RNA is isolated from the cell lysates that have been kept at −80° C. using the Promega kit ReliaPrep RNA Cell Miniprep System. Total RNA is quantified using a Nanodrop 2000 spectrophotometer.

400 ng of RNA is used as template for the cDNA synthesis using the Verso cDNA synthesis kit (Thermoscientific) according to the manufacturer's instructions.

cDNA is diluted 2.5× for this reaction and 2 µl of these diluted cDNA is used as template. Amplification of the target sequence uses AMPLITAQ GOLD® 360 DNA Polymerase from Life Technologies. Primers used are ex26_Fw (SEQ ID NO: 10) and ex27_Rv (SEQ ID NO: 11) with PCR conditions as follows: hold 5 min at 95° C., denature 30 sec at 95° C., anneal 30 sec at 58° C. and extend 35 sec at 72° C., 35 cycles, final extension is 7 min at 72° C.

PCR fragments are analyzed in the Agilent 2100 Bioanalyzer using the Agilent DNA 1000 Kit from Agilent technologies. This kit contains a chip composed of interconnected microchannels, through which the fragments are separated based on their size as they are driven through it electrophoretically. To measure the level of expression of CEP290 mRNA, wild type and mutant transcripts are amplified as 93 bp and 117 bp fragments, respectively. The human PO large ribosomal protein mRNA (RPLP0) is used as normalization. The primers used are wt_Fw (SEQ ID NO: 12), wt-Rv (SEQ ID NO: 13), mt_Fw (SEQ ID NO: 14), and mt_Rv (SEQ ID NO: 15). For this reaction, SYBR select master mix from Life Technologies along with cDNA diluted 10× used as template. PCR program is 50° C. for 2 min, 95° C. for 2 min, 50 cycles of 95° C. for 15 sec, 62.5° C. for 1 min.

Example 3: Reversing an Amino Acid Substitution in a Mutant CFTR G551D Target RNA by Site-Directed A to I Editing Oligonucleotide construct to be used: 5'-cgcgcgttttcgcgcg CGUUGAC*CUCCACUC-3' (SEQ ID NO: 3)

The cell lines are human fibroblasts, generated from skin and heart pericardium biopsies, GM00142 and GM03465, respectively, Coriell Institute Cell Repository). They are both heterozygote: one allele carries the deltaF508 deletion mutation (Phe508Del) and a second allele carries a G-to-A transition at nucleotide 1784 (1784G>A) which converts the gly-551 codon (GGT) to an asp (GAT), resulting in a missense mutation in exon 11 in the CFTR gene [Gly551Asp (G551D)]. All cell lines are grown in Eagle's Minimum Essential Medium (Life Technologies) with Earle's salts and non-essential amino acids supplemented with 15% FBS non-activated and 1% Pen/strep.

A day before transfection, cells are seeded in a density of 2×10⁵/well on a 6-well plate in a total volume of 2.5 ml of medium. The day of the transfection, the oligo to be tested is added to each well in a final concentration of 100 nM using maxPEI (Poliscience) as a transfection agent, with a mass ratio oligo:PEI of 1:4. After 24 h, cells are washed with PBS and cell lysate is collected and frozen at −80° C.

RNA is isolated from the cell lysates that have been kept at −80° C. using the Promega kit ReliaPrep RNA Cell Miniprep System. Total RNA is quantified using a Nanodrop 2000 spectrophotometer. 400 ng of RNA is used as template for the cDNA synthesis using the Verso cDNA synthesis kit (Thermoscientific) according to the manufacturer's instructions. 1 µl of cDNA was first subjected to PCR with 0.4 µM of forward and reverse primers, 25 µM of each dNTP, 1×AMPLITAQ GOLD® 360 Buffer, 3.125 30 mM MgCl2 and 1.0 units of AMPLITAQ GOLD® 360 polymerase (all Life Technologies) were assembled. The primers used are SEQ ID NOs: 26 (fwd) and 27 (rev). The PCR cycles were performed using the following cycling conditions. An initial denaturing step at 95° C. for 7 min was followed by 30 cycles of 30 s at 95° C., 30 s at 55° C. and 45 s at 72° C. The PCR amplifications were terminated by a final elongation period of 7 min at 72° C. 1 µl of the previous PCR was used in a nested-PCR program containing 35 0.4 µM of forward primers and a unique MiSeq index primer per sample, 25 µM of each dNTP, 1×AMPLITAQ GOLD® 360 Buffer, 3.125 mM MgCl₂ and 1.0 units AMPLITAQ GOLD® 360 polymerase. PCR cycles were performed using the following cycling conditions: an initial denaturing step at 95° C. for 7 min was followed by 25 cycles of 30 s at 95° C., 30 s at 60° C. and 45 s at 72° C. Reactions were terminated using a final elongation period of 7 minutes at 72° C. Before loading the PCR products containing the MiSeq sequence primer sequences in the sequencer, the concentration of the purified PCR products was measured using a QUBIT® 2.0 Fluorometer (Life Technologies) according the manufacturer's protocol. In summary, two Assay Tubes for the standards were made by making 20-fold dilutions of the 2 stock standards in working solution. For each sample, 200 µl of working solution was prepared in 10 separate tubes, 1 µl of the PCR product was brought into this solution and mixed by vortexing for a couple of seconds. Samples were measured against the two standards and the concentration in ng/µl was calculated accordingly. Sequencing of the PCR products was performed on the MISEQ™ system from Illumina, which uses sequencing-by-synthesis to provide rapid high quality sequence data.

Example 4: Reversing an Amino Acid Substitution Mutation in the α-1-Antitrypsin (A1AT) Transcript by Targeted A to I Editing for the Treatment of A1AT Deficiency

```
Oligonucleotides:
ADAR45:
                                       (SEQ ID NO: 28)
rGrGrArArUrArGrUrArUrArArCrArArUrArUrgrcrurararA rUrGrUrUrGrUrUrArUrArGrUrArUrCrCrCmC*mA*mG*mU*mC mCmCmUmUmUmCrUrCrGmUmCmGmAmUmGmG*mU*mC*mA*mG ADAR47:
                                       (SEQ ID NO: 28)
mG*mG*mA*mA*mU*mA*mG*mU*mA*mU*mA*mA*mC*mA*mA*mU* mA*mU*mG*mC*mU*mA*mA*mA*mU*mG*mU*mU*mG*mU*mU*mA* mU*mA*mG*mU*mA*mU*mC*mC*mCmC*mA*mG*mU*mCmCmCmUmU mUmCrUrCrGmUmCmGmAmUmGmG*mU*mC*mA*mG
r = no modification
m = 2'O-Me
*= phosphorothioate linkage
```

Transfection of Liver Fibroblasts

Liver fibroblasts are provided from Coriell Cell Repository (GM11423), isolated from a donor subject homozygous for the Z allele (ZZ), which results from a G>A transition at nucleotide 9989 in exon 5 of the SERPINA1 gene [9989G>A] resulting in a substitution of lysine for glutamic acid at codon 342 [Glu342Lys (E342K)]. The cells are maintained in EMEM medium (Life Technologies) and supplemented with 15% FBS. One day before the transfections the cells are seeded in a 6-well plate in a total volume of 2 ml of medium. On the day of the transfection oligonucleotide is added to 1×PBS (Thermo Fisher Scientific) in 1.5 ml microfuge tube and mixed with MaxPei (Polysciences) and incubated together and incubated for 20 min. In the meantime, cell culture medium is removed from the cells and suitable amount of fresh EMEM with 15% FBS is added. Then DNA/Oligo-MaxPei diluted mixture is added on to the cell with gentle drop by drop pipetting. The cells are incubated at 37° C. and the medium is refreshed after 6-24 h.

RNA Isolation

RNA Isolation is performed using the Reliaprep RNA Cell Miniprep System (Promega) according to the manufacturer's procedure. Briefly, culture medium is removed and the cells are washed with cold PBS. 250 µl lysis buffer is added on each well of 6-well plate. The plate is gently rocked and the cells are lysed completely by repeated pipetting over the well surface. 85 µl isopropanol is added on to the lysate as recommended and the lysate is transferred to Minicolumn and centrifuged for 30 sec at 12,000-14,000 g (RT), the liquid is discarded. 500 µl of RNA Wash Solution is added and centrifuged again 30 sec at 12,000-14,000 g. In a sterile tube, DNase I incubation master mix is prepared by combining sample 24 µl of Yellow Core Buffer, 3 µl 0.09M $MnCl_2$, 3 µl DNAse I and 30 µl freshly prepared DNase I mix is added to the membrane in the column of each sample, incubated for 15 min at RT. Then 200 µl of Column Wash Solution is added and centrifuged for 15 sec at 12,000-14,000 g. After that 500 µl of RNA Wash Solution is added and centrifuged for 30 sec at 12,000-14,000 g and liquid is discarded. The minicolumn is placed into a new collection tube and 300 µl of RNA Wash Solution is added and centrifuged at 14,000 g for 2 min. Each Minicolumn is placed to an Elution Tube and Nuclease-Free Water is added to the membrane and centrifuged 1 min. Lastly, RNA concentration is measured on the Nanodrop.

cDNA Synthesis cDNA synthesis is performed using the Verso cDNA synthesis kit (Thermo Fisher) with 500 ng or 1000 ng RNA input. RNA mix is prepared by taking the desired amount of RNA and completing it to a total volume of 11 µl by adding water. The mix is heated for 5 min. at 70° C., then cooled. cDNA mix is prepared according to the pipetting scheme provided by the supplier. 9 µl of cDNA mix is put in a reaction tube and 11 µl RNA mix is added and is kept at the thermal cycler for 30 min. at 42° C. and 2 min. at 95° C.

PCR

PCR is performed using the AMPLITAQ GOLD® 360 DNA Polymerase 1000U Kit (Applied Biosystems). A PCR mastermix is prepared by adding 1 µl of cDNA, 2.5 µl of 10× buffer, 3 µl of $MgCl_2$, 0.5 µl of dNTPs, 1 µl of each primer, 0.5 µl Taq polymerase and by adding water to complete 25 µl. The PCR program is as follows; 95° C. for 5 min, 95° C. for 30 s, 55° C. for 30 s, 72° C. for 1 min for 35 cycles and 72° C. for 7 min. After PCR, the samples are run on the Bioanalyzer using the DNA 1000 kit (Agilent) and program.

PCR Sample Purification

Samples are purified using a Nucleospin PCR cleanup kit (Macherey-Nagel) to ensure removal of contamination of PCR products. 1 volume of PCR sample is mixed with 2 volumes NT1 and samples are loaded into the NUCLEOSPIN® Gel and PCR Clean-up Column is placed in a Collection Tube and centrifuged for 30 s at 11000× g. The liquid is discarded and column is placed back into collection tube. 700 µl Buffer NT3 to the NUCLEOSPIN® Gel is added and centrifuged for 30 s at 11000×g. The washing step is repeated and tubes are centrifuged for 1 min at 11000×g to remove Buffer NT3.

NUCLEOSPIN® Gel and PCR Clean-up Column is placed into a new 1.5 ml Eppendorf tube, 15-30 µl Buffer NE is added and incubated for 1 min. at room temperature then centrifuged for 1 min. at 11000×g. DNA concentration is measured by using the Nanodrop method.

Restriction Digestion

After PCR clean up, SERPINA1 amplicon is subjected to Hyp99I restriction digestion. The enzyme recognizes the last G in CGACG sequence in WT and cuts the amplicon in two pieces but it cannot cut CGACA sequence in the mutant version because of absence of the second G. Thus if editing is successful there will be some WT DNA as a substrate for Hyp99I restriction digestion. 1 unit of Hyp99I (NEB) is used to digest 0.1 µg of DNA. A DNA input of 0.5 µg is used. Samples are diluted in nuclease-free water and incubated for 1-1.5 hour at 37° C., the enzyme is inactivated by subsequent incubation of the samples at 65° C. for 20 min. After incubation, samples are loaded on the Bioanalyzer using the DNA1000 kit (Agilent) and program to visualize the results.

Taqman PCR

SNP genotyping assay is performed using the custom SERPINA1 SNP genotyping assay (ThermoFisher Scientific). This assay is performed in parallel to restriction enzyme digestion assay to explore which assay is more sensitive for the detection of editing. The probes specific to WT and mutant SERPINA1 have different fluorescent groups attached, VIC and FAM, respectively. So we can quantify the increase or decrease in the amounts of WT/mutant transcripts. The reaction mix is prepared by adding 5 µl of master mix and 0.5 µl of probe-primer mixture. Sequences of oligos used are: WT probe (SEQ ID NO: 29), mutant probe (SEQ ID NO: 30), forward primer (SEQ ID NO: 31), and reverse primer (SEQ ID NO: 32). 5.5 µl reaction mix is added to the designated wells of a 96-well plate. 4.5 µl of cDNA is added to each well. The PCR program is run as follows: 95° C. for 10 min, 92° C. for 15 sec and 60° C. for 90 sec for 50 cycles. The results were analyzed by using the CFX Manager.

Example 5: Reversing an Amino Acid Substitution Mutation G2019S in the LRRK2 Transcript by Targeted A to I Editing for the Treatment of Parkinson's Disease Mutations in the catalytic Roc-COR and kinase domains of leucine-rich repeat kinase 2 gene (LRRK2 Gene ID: 120892) are a common cause of familial Parkinson's disease (PD). We set out to target the G2019S mutation in the LRRK2 pre-mRNA transcript (Transcript RefSeq NM_198578.3) using AONs capable of recruiting ADAR1 and 2 by virtue of the full length or shortened GluRB portion as recruiting portion linked to a targeting portion with complementarity to the sequence surrounding the G to A mutation in exon 41 at position G6055 (see sequence below with the mutated G underlined). This mutation is also identified as Genbank dbSNP variation rs34637584, commonly referred to as G2019S.

LRRK2 Exon 41 Sequence with the Wt G Residue Highlighted in Position 6055:

(SEQ ID NO: 33)
ATACCTCCACTCAGCCATGATTATATACCGAGACCTGAAACCCCACAATG

TGCTGCTTTTCACACTGTATCCCAATGCTGCCATCATTGCAAAGATTGCT

GACTACGGCATTGCTCAGTACTGCTGTAGAATGGGGATAAAAACATCAGA

GGGCACACCAG

Mutant Allele and Translation:

SEQ ID NO: 34
GCT GAC TAC AGC ATT GCT CAG

SEQ ID NO: 35
Ala Asp Tyr Ser Ile Ala Gln

Normal Allele and Translation (after A to I Editing):

SEQ ID NO: 36
GCT GAC TAC GGC ATT GCT CAG

SEQ ID NO: 37
Ala Asp Tyr Gly Ile Ala Gln

The following sequences have been designed to target the LRRK2 G2019S mutation. Nucleotides in bold form the targeting portion; all nucleotides are 2'-OMe except those underlined; * designates a PS-linkage. The AONs vary in the length of the targeting portion either 25 (LRRK2-ADAR1 and LRRK2-ADAR3) or 30 nucleotides (LRRK-ADAR2 and 4). The AONs vary in the length of the recruiting portion: shortened GluRB recruiting portion (LRRK2-ADAR3 and 4) and full length GluRB recruiting portion (LRRK2-ADAR1 and 2).

| LRRK2- | Sequence (SEQ ID NO:) |
|---|---|
| ADAR1 | GUGGAAUAGUAUAACAAUAUgcuaaAUGUUGUUAUAGUA UCCCACACUGAGCAAUGCcGUAGUCAG\*C\*A\*A\*U (SEQ ID NO: 38) |
| ADAR2 | GUGGAAUAGUAUAACAAUAUgcuaaAUGUUGUUAUAGUA UCCCACGUACUGAGCAAUGCcGUAGUCAGCAA\*U\*C\*U\*U (SEQ ID NO: 39) |
| ADAR3 | GGAAUAGUAUAACAAUAUgcuaaAUGUUGUUAUAGUAUC CCACUGAGCAAUGCcGUAGUCAG\*C\*A\*A\*U (SEQ ID NO: 40) |
| ADAR4 | GGAAUAGUAUAACAAUAUgcuaaAUGUUGUUAUAGUAUC CCGUACUGAGCAAUGCcGUAGUCAGCAA\*U\*C\*U\*U (SEQ ID NO: 41) |

Correction of LRRK2 is assessed in LRRK2G6055A mutant fibroblasts through means of RNA sequencing, western blot analysis of LRRK2 (auto)-phosphorylation status, and functional readouts of established LRRK2-associated mitochondrial phenotypes (oxygen consumption rate and mitochondrial membrane potential). See: Tatiana et al. (2012) Hum. Mol. Genet. 21 (19): 4201-4213; Smith et al. (2015) Molecular Neurobiology, 1-17; and Grünewald et al. (2014) Antioxidants & Redox Signaling, 20(13), 1955-1960.

LRRK2G6055A homozygous fibroblast line fff-028 (Telethon Network of Genetic Biobanks), heterozygous G6055A lines ND29492, ND29542, ND29802, and healthy controls lines GM023074, GM08402 (Coriell Institute), are transfected with LRRK2-ADAR AON using Lipofectamine 2000. After 48-96 hours incubation, the following analyses are performed:

1) To detect A-to-I edited LRRK2 transcript, cells are lysed, RNA isolated by standard methods, and subjected to semi-quantitative RNA sequencing analysis using the following sequencing primers of SEQ ID NOs: 42 & 43. A-to-I edited mRNA sequences appear after transfection of LRRK2-ADAR-AON.

2) LRRK2G6055A protein has previously been demonstrated (Smith et al., 2015) to show increased auto-phosphorylation at serine 955 after stress-treatment with the mitochondrial membrane depolarizing agent valinomycin (10 µM for 24 h), due to increased catalytic activity of the kinase domain, as compared to LRRK2 wt. Treatment with LRRK2-ADAR-AON reduces serine-955 phosphorylation of valinomycin-treated LRRK2G6055A cells at least partially, potentially even completely to wild-type levels. This can be assessed by western blot analysis (Smith et al.) using LRRK2 phospho-5955 (Abcam clone MJF-R11-(75-1)), and total LRRK2 (Abcam clone MJFF2 (c41-2)) antibodies.

3) LRRK2G6055A fibroblasts display alterations in mitochondrial respiration (OXPHOS), including increased proton leak (Smith et al., 2015; Grünewald et al., 2014) which can be reversed after LRRK2-ADAR-AON transfection. Oxygen consumption rate under basal and forced respiratory conditions is assessed using a Seahorse XF24 extracellular flux analyzer (Seahorse Bioscience), a device that measures concentration of dissolved oxygen in the culture medium in 2 s time intervals by solid-state sensor probes. This analysis can be performed together with XF Xell Mito Stress Test kit (Seahorse Bioscience), which by sequential treatment with oligomycin, carbonyl cyanide-4-(trifluoromethoxy)phenyl hydrazone (FCCP), rotenone and antimycin-A, can determine metabolic parameters such as basal respiration, ATP production, proton leak, and maximal respiration. The assay is performed according to manufacturer's instructions, and proton leak is defined as remaining oxygen consumption after oligomycin treatment.

4) LRRK2G6055A fibroblasts display decreased mitochondrial membrane potential as compared to control cells (Smith et al., 2015; Grünewald et al., 2014). Mitochondrial membrane potential is assessed with the lipophilic cationic dye tetramethylrhodamine methylester (TMRM), used in non-quenching mode (0.5-30 nM, determined empirically), loaded in phenol red-free culture medium for 20 minutes. After dye-loading, steady-state mitochondrial TMRM fluorescence is measured by live-cell confocal microscopy and image analysis. LRRK2-ADAR-AON transfection can increase mitochondrial membrane potential at least partially, potentially even completely to control levels.

CONCLUSIONS

The examples described above show how to make desired changes in a target RNA sequence by site-directed editing of nucleotides in a target RNA molecule using oligonucleotide constructs according to the invention. The examples teach how to remove a stop codon to reopen the reading frame of a GFP expression construct, create a splice site to change the splicing pattern of the target RNA coding for CEP290, and how to establish a desired amino acid substitution by making a change in a codon in the target RNA sequence coding for a mutant G551D CFTR protein. Successful RNA editing can conveniently be confirmed, for example by observing fluorescent cells in the case of the GFP non-sense mutation reversal, by observing a shift in the RT-PR bands in a gel from wild-type to mutant in the case of introducing the cryptic splice site in the CEP290 coding RNA, and by sequencing, or by using a functional assay (e.g. an Ussing chamber assay), in the case of the reversal of the G551D mutation in the CFTR coding RNA, and the like. Similar work on α-1-antitrypsin (A1AT) and LRRK2 can also be performed.

It will be understood that the invention is described above by way of example only and modifications may be made whilst remaining within the scope and spirit of the invention.

SEQUENCES
SEQ ID NO: 1 DNA-RNA oligonucleotide construct editing a non-sense mutation in eGFP:
cgcgcgttttcgcgcgGCUGAACCACUGCAC SEQ ID NO: 2 DNA-RNA oligonucleotide construct creating a cryptic splice site in hCEP290:
cgcgcgttttcgcgcgGAGAUACUCACAAUU SEQ ID NO: 3 DNA-RNA Oligonucleotide construct editing a G551D mutation in hCFTR:
cgcgcgttttcgcgcgCGUUGACCUCCACUC SEQ ID NO: 4 hCFTR DNA showing G551D hCFTR mutation in lower case (n is T or C):
ATGCAGAGGTCGCCTCTGGAAAAGGCCAGCGTTGTCTCCAAACTTTTTTTCAGCTGGACCAGACCAATTTTGAGGAAAGGATACAG ACAGCGCCTGGAATTGTCAGACATATACCAAATCCCTTCTGTTGATTCTGCTGACAATCTATCTGAAAAATTGGAAAGAGAATGGG ATAGAGAGCTGGCTTCAAAGAAAAATCCTAAACTCATTAATGCCCTTCGGCGATGTTTTTTCTGGAGATTATGTTCTATGGAATC TTTTTATATTTAGGGGAAGTCACCAAAGCAGTACAGCCTCTCTTACTGGGAAGAATCATAGCTTCCTATGACCCGGATAACAAGGA GGAACGCTCTATCGCGATTTATCTAGGCATAGGCTTATGCCTTCTCTTTATTGTGAGGACACTGCTCCTACACCCAGCCATTTTTG GCCTTCATCACATTGGAATGCAGATGAGAATAGCTATGTTTAGTTTGATTTATAAGAAGACTTTAAAGCTGTCAAGCCGTGTTCTA GATAAAATAAGTATTGGACAACTTGTTAGTCTCCTTTCCAACAACCTGAACAAATTTGATGAAGGACTTGCATTGGCACATTTCGT GTGGATCGCTCCTTTGCAAGTGGCACTCCTCATGGGGCTAATCTGGGAGTTGTTACAGGCGTCTGCCTTCTGTGGACTTGGTTTCC TGATAGTCCTTGCCCTTTTTCAGGCTGGGCTAGGGAGAATGATGATGAAGTACAGAGATCAGAGAGCTGGGAAGATCAGTGAAAGA CTTGTGATTACCTCAGAAATGATTGAAAATATCCAATCTGTTAAGGCATACTGCTGGGAAGAAGCAATGGAAAAAATGATTGAAAA CTTAAGACAAACAGAACTGAAACTGACTCGGAAGGCAGCCTATGTGAGATACTTCAATAGCTCAGCCTTCTTCTTCTCAGGGTTCT TTGTGGTGTTTTTATCTGTGCTTCCCTATGCACTAATCAAAGGAATCATCCTCCGGAAAATATTCACCACCATCTCATTCTGCATT GTTCTGCGCATGGCGGTCACTCGGCAATTTCCCTGGGCTGTACAAACATGGTATGACTCTCTTGGAGCAATAAACAAATACAGGA TTTCTTACAAAAGCAAGAATATAAGACATTGGAATATAACTTAACGACTACAGAAGTAGTGATGGAGAATGTAACAGCCTTCTGGG AGGAGGGATTTGGGGAATTATTTGAGAAAGCAAACAAAACAATAACAATAGAAAAACTTCTAATGGTGATGACAGCCTCTTCTTC AGTAATTTCTCACTTCTTGGTACTCCTGTCCTGAAAGATATTAATTTCAAGATAGAAAGAGGACAGTTGTTGGCGGTTGCTGGATC CACTGGAGCAGGCAAGACTTCACTTCTAATGATGATTATGGGAGAACTGGAGCCTTCAGAGGGTAAAATTAAGCACAGTGGAAGAA TTTCATTCTGTTCTCAGTTTTCCTGGATTATGCCTGGCACCATTAAAGAAAATATCAT<u>CTT</u>TGGTGTTTCCTATGATGAATATAGA TACAGAAGCGTCATCAAAGCATGCCAACTAGAAGAGGACATCTCCAAGTTTGCAGAGAAAGACAATATAGTTCTTGGAGAAGGTGG AATCACACTGAGTGGAanCAACGAGCAAGAATTTCTTTAGCAAGAGCAGTATACAAAGATGCTGATTTGTATTTATTAGACTCTC CTTTTGGATACCTAGATGTTTTAACAGAAAAAGAAATATTTGAAAGCTGTGTCTGTAAACTGATGGCTAACAAAACTAGGATTTTG GTCACTTCTAAAATGGAACATTTAAAGAAAGCTGACAAAATATTAATTTTGCATGAAGGTAGCAGCTATTTTTATGGGACATTTTC AGAACTCCAAAATCTACAGCCAGACTTTAGCTCAAAACTCATGGGATGTGATTCTTTCGACCAATTTAGTGCAGAAAGAAGAAATT CAATCCTAACTGAGACCTTACACCGTTTCTCATTAGAAGGAGATGCTCCTGTCTCCTGGACAGAAACAAAAAAACAATCTTTTAAA CAGACTGGAGAGTTTGGGGAAAAAAGGAAGAATTCTATTCTCAATCCAATCAACTCTATACGAAAATTTTCCATTGTGCAAAAGAC TCCCTTACAAATGAATGGCATCGAAGAGGATTCTGATGAGCCTTTAGAGAGAAGGCTGTCCTTAGTACCAGATTCTGAGCAGGGAG AGGCGATACTGCCTCGCATCAGCGTGATCAGCACTGGCCCCACGCTTCAGGCACGAAGGAGGCAGTCTGTCCTGAACCTGATGACA CACTCAGTTAACCAAGGTCAGAACATTCACCGAAAGACAACAGCATCCACACGAAAAGTGTCACTGGCCCCTCAGGCAAACTTGAC TGAACTGGATATATATTCAAGAAGGTTATCTCAAGAAACTGGCTTGGAAATAAGTGAAGAAATTAACGAAGAAGACTTAAAGGAGT GCTTTTTTGATGATATGGAGAGCATACCAGCAGTGACTACATGGAACACATACCTTCGATATATTACTGTCCACAAGAGCTTAATT TTTGTGCTAATTTGGTGCTTAGTAATTTTTCTGGCAGAGGTGGCTGCTTCTTTGGTTGTGCTGTGGCTCCTTGGAAACACTCCTCT TCAAGACAAAGGGAATAGTACTCATAGTAGAAATAACAGCTATGCAGTGATTATCACCAGCACCAGTTCGTATTATGTGTTTTACA TTTACGTGGGAGTAGCCGACACTTTGCTTGCTATGGGATTCTTCAGAGGTCTACCACTGGTGCATACTCTAATCACAGTGTCGAAA ATTTTACACCACAAAATGTTACATTCTGTTCTTCAAGCACCTATGTCAACCCTCAACACGTTGAAAGCAGGTGGGATTCTTAATAG ATTCTCCAAAGATATAGCAATTTTGGATGACCTTCTGCCTCTTACCATATTTGACTTCATCCAGTTGTTATTAATTGTGATTGGAG -continued

```
CTATAGCAGTTGTCGCAGTTTTACAACCCTACATCTTTGTTGCAACAGTGCCAGTGATAGTGGCTTTTATTATGTTGAGAGCATAT
TTCCTCCAAACCTCACAGCAACTCAAACAACTGGAATCTGAAGGCAGGAGTCCAATTTTCACTCATCTTGTTACAAGCTTAAAAGG
ACTATGGACACTTCGTGCCTTCGGACGGCAGCCTTACTTTGAAACTCTGTTCCACAAAGCTCTGAATTTACATACTGCCAACTGGT
TCTTGTACCTGTCAACACTGCGCTGGTTCCAAATGAGAATAGAAATGATTTTGTCATCTTCTTCATTGCTGTTACCTTCATTTCC
ATTTTAACAACAGGAGAAGGAGAAGGAAGAGTTGGTATTATCCTGACTTTAGCCATGAATATCATGAGTACATTGCAGTGGGCTGT
AAACTCCAGCATAGATGTGGATAGCTTGATGCGATCTGTGAGCCGAGTCTTTAAGTTCATTGACATGCCAACAGAAGGTAAACCTA
CCAAGTCAACCAAACCATACAAGAATGGCCAACTCTCGAAAGTTATGATTATTGAGAATTCACACGTGAAGAAAGATGACATCTGG
CCCTCAGGGGGCCAAATGACTGTCAAAGATCTCACAGCAAAATACACAGAAGGTGGAAATGCCATATTAGAGAACATTTCCTTCTC
AATAAGTCCTGGCCAGAGGGTGGGCCTCTTGGGAAGAACTGGATCAGGGAAGAGTACTTTGTTATCAGCTTTTTTGAGACTACTGA
ACACTGAAGGAGAAATCCAGATCGATGGTGTGTCTTGGGATTCAATAACTTTGCAACAGTGGAGGAAAGCCTTTGGAGTGATACCA
CAGAAAGTATTTATTTTTTCTGGAACATTTAGAAAAAACTTGGATCCCTATGAACAGTGGAGTGATCAAGAAATATGGAAAGTTGC
AGATGAGGTTGGGCTCAGATCTGTGATAGAACAGTTTCCTGGGAAGCTTGACTTTGTCCTTGTGGATGGGGCTGTGTCCTAAGCC
ATGGCCACAAGCAGTTGATGTGCTTGGCTAGATCTGTTCTCAGTAAGGCGAAGATCTTGCTGCTTGATGAACCCAGTGCTCATTTG
GATCCAGTAACATACCAAATAATTAGAAGAACTCTAAAACAAGCATTTGCTGATTGCACAGTAATTCTCTGTGAACACAGGATAGA
AGCAATGCTGGAATGCCAACAATTTTTGGTCATAGAAGAGAACAAAGTGCGGCAGTACGATTCCATCCAGAAACTGCTGAACGAGA
GGAGCCTCTTCCGGCAAGCCATCAGCCCCTCCGACAGGGTGAAGCTCTTTCCCCACCGGAACTCAAGCAAGTGCAAGTCTAAGCCC
CAGATTGCTGCTCTGAAAGAGGAGACAGAAGAAGAGGTGCAAGATACAAGGCTT

SEQ ID NO: 5 - example recruiting portion
CGCGCGTTTTCGCGCG

SEQ ID NO: 6 - example recruiting portion
AUANUAUAACAAUAUgcuaaAUGUUGUUAUANUAU

SEQ ID NO: 7 - example recruiting portion
UAUAACAAUAUgcuaaAUGUUGUUAUA

SEQ ID NO: 8 - generic targeting portion
NNNNNNNNNNNNNNNNNCNNN

SEQ ID NO: 9
GCAACUAGAGGUGAG

SEQ ID NO: 10
TGCTAAGTACAGGGACATCTTGC

SEQ ID NO: 11
AGACTCCACTTGTTCTTTTAAGGAG

SEQ ID NO: 12
TGACTGCTAAGTACAGGGACATCTTG

SEQ ID NO: 13
AGGAGATGTTTTCACACTCCAGGT

SEQ ID NO: 14
CTGGCCCCAGTTGTAATTTGTGA

SEQ ID NO: 15
CTGTTCCCAGGCTTGTTCAATAGT

SEQ ID NO: 16
GUGUUGGCCAUGGAACAUAUAACAAUAUgcuaaAUGUUGUUAUA

SEQ ID NO: 17
UAUAACAAUAUgcuaaAUGUUGUUAUAGUGUUGGCCAUGGAACA

SEQ ID NO: 18
GUGUUGGCCAUGGAACAUAUAACAAUAUgcuaaAUGUUGUUAUA

SEQ ID NO: 19
GUGUUGGCCAUGGAACAAUAGUAUAACAAUAUgcuaaAUGUUGUUAUAGUAU

SEQ ID NO: 20
```

-continued

GGAAUAGUAUAACAAUAUGcuaaAUGUUGUUAUAGUAUCCCGUGUUGGCCAUGGAACA

SEQ ID NO: 21
GUGUUGGCCAUGGAACAGGAAUAGUAUAACAAUAUgcuaaAUGUUGUUAUAGUAUCCC

SEQ ID NO: 22
GGAAUAGUAUAACAAUAUgcuaaAUGUUGUUAUAGUAUCCCGUGUUGGCCAUGGAACA

SEQ ID NO: 23
GGAAUANUAUAACAAUAUgcuaaAUGUUGUUAUANUAUCCC

SEQ ID NO: 24
GUGGAAUANUAUAACAAUAUgcuaaAUGUUGUUAUANUAUCCCAC

SEQ ID NO: 25
GUGGNAUANUAUAACAAUAUgcuaaAUGUUGUUAUANUAUNCCAC

SEQ ID NO: 26
GCCTGGCACCATTAAAGAAA

SEQ ID NO: 27
GCATCTTTGTATACTGCTCTTGCT

SEQ ID NO: 28
GGAAUAGUAUAACAAUAUgcuaaAUGUUGUUAUAGUAUCCCAGUCCCUUUCUCGUCGAUGGUCAG

SEQ ID NO: 29
CCATCGACGAGAAAG

SEQ ID NO: 30
CAT CGACAAGAAAG

SEQ ID NO: 31
TCCAGGCCGTGCATAAGG

SEQ ID NO: 32
GCCCCAGCAGCTTCAG

SEQ ID NO: 33
ATACCTCCACTCAGCCATGATTATATACCGAGACCTGAAACCCCACAATGTGCTGCTTTTCACACTGTATCCCAATGCTGCCATCA

TTGCAAAGATTGCTGACTACGGCATTGCTCAGTACTGCTGTAGAATGGGGATAAAAACATCAGAGGGCACACCAG

SEQ ID NO: 34
GCTGACTACAGCATTGCTCAG

SEQ ID NO: 35
ADYSIAQ

SEQ ID NO: 36
GCTGACTACGGCATTGCTCAG

SEQ ID NO: 37
ADYGIAQ

SEQ ID NO: 38
GUGGAAUAGUAUAACAAUAUgcuaaAUGUUGUUAUAGUAUCCCACACUGAGCAAUGCcGUAGUCAGCAAU SEQ ID NO: 39
GUGGAAUAGUAUAACAAUAUgcuaaAUGUUGUUAUAGUAUCCCACGUACUGAGCAAUGCcGUAGUCAGCAAUCUU SEQ ID NO: 40
GGAAUAGUAUAACAAUAUgcuaaAUGUUGUUAUAGUAUCCCACUGAGCAAUGCcGUAGUCAGCAAU SEQ ID NO: 41
GGAAUAGUAUAACAAUAUgcuaaAUGUUGUUAUAGUAUCCCGUACUGAGCAAUGCcGUAGUCAGCAAUCUU

SEQ ID NO: 42
GTTTGAGATACCTCCACTCAGC

SEQ ID NO: 43
AGGTGCACGAAACCCTGGTG

The invention claimed is:

1. A method for making a change in a target RNA sequence in a human cell, comprising the steps of:
   (i) introducing into the cell an oligonucleotide construct that is sufficiently complementary to the target RNA sequence, wherein the target RNA sequence comprises a target adenosine;
   (ii) allowing the formation of a double-stranded structure of the oligonucleotide construct with the target RNA sequence upon base pairing;
   (iii) allowing the double-stranded structure of the oligonucleotide and the target RNA sequence to recruit an hADAR1 or hADAR2 enzyme that is naturally present in the cell; and
   (iv) allowing the hADAR1 or hADAR2 enzyme to perform an editing reaction on the target adenosine in the target RNA sequence,
   wherein the oligonucleotide construct comprises a cytidine opposite the target adenosine.

2. The method of claim 1, further comprising the step of:
   (v) identifying the presence of the change in the target RNA sequence.

3. The method of claim 1, wherein the cytidine opposite the target adenosine is not 2'-OMe modified.

4. The method of claim 3, wherein at least one nucleotide in the oligonucleotide construct comprises a 2'-O modified ribose.

5. The method of claim 4, wherein the 2'-O modified ribose is modified by a substitution with a lower alkyl (C1-4), an alkenyl (C2-4), an alkynyl (C2-4), an alkoxy alkyl, a 3,3'-dimethylallyl, or a locked nucleic acid group.

6. The method of claim 4, wherein the 2'-O modified ribose is modified by a substitution with 2'-OMe or 2'-MOE.

7. The method of claim 1, wherein a phosphodiester group of the backbone of the oligonucleotide construct is modified by a phosphorothioate, phosphorodithioate, or phosphoroamidate internucleoside linkage.

8. The method of claim 1, wherein the oligonucleotide construct is between 20 and 100 nucleotides in length, between 24 and 60 nucleotides in length, or between 30 and 50 nucleotides in length.

9. The method of claim 1, wherein the change in the target RNA sequence is conducted in vivo or ex vivo.

10. The method of claim 1, wherein the change in the target RNA sequence treats a genetic disease in a human subject in need thereof wherein the genetic disease is selected from the group consisting of alpha-1-antitrypsin deficiency, Hurler Syndrome, and Parkinson's disease.

11. The method of claim 1, wherein the human cell is a skin cell, a lung cell, a heart cell, a kidney cell, a liver cell, a pancreas cell, a gut cell, a muscle cell, a gland cell, an eye cell, a brain cell, or a blood cell.

12. The method of claim 1, wherein the human cell is a stem cell.

13. The method of claim 12, wherein the stem cell is an embryonic stem cell, a pluripotent stem cell, a totipotent stem cell, or an induced pluripotent stem cell.

14. The method of claim 1, wherein the target RNA sequence is selected from a pre-messenger RNA, a messenger RNA, a ribosomal RNA, a transfer RNA, or a miRNA.

15. The method of claim 1, wherein at least one nucleotide in the oligonucleotide construct comprises a chemical modification.

16. The method of claim 1, wherein the oligonucleotide construct is formulated for intravenous administration.

17. A method for making a change in a target RNA sequence in a human cell, comprising the steps of:
   (i) introducing into the cell an oligonucleotide construct that is sufficiently complementary to bind by nucleobase pairing to the target RNA sequence, wherein the target RNA sequence comprises a target adenosine;
   (ii) allowing the formation of a double-stranded structure of the oligonucleotide construct with the target RNA sequence upon base pairing;
   (iii) allowing the double-stranded structure of the oligonucleotide and the target RNA sequence to recruit an hADAR1 or hADAR2 enzyme naturally present in the cell; and
   (iv) allowing the hADAR1 or hADAR2 enzyme to perform deamination of the target adenosine to an inosine in the target RNA sequence.

18. The method of claim 17, wherein the oligonucleotide construct comprises one or more mismatches or wobble bases with the complementary target RNA sequence.

19. A method for making a change in a target RNA sequence in a human cell, comprising the steps of:
   (i) introducing into the cell an oligonucleotide construct that has sufficient overlap and complementarity to the target RNA sequence, wherein the target RNA sequence comprises a target adenosine;
   (ii) allowing the formation of a double-stranded structure of the oligonucleotide construct with the target RNA sequence upon base pairing;
   (iii) allowing the double-stranded structure of the oligonucleotide and the target RNA sequence to recruit an hADAR1 or hADAR2 enzyme naturally present in the cell; and
   (iv) allowing the hADAR1 or hADAR2 enzyme to perform an editing reaction on the target adenosine in the target RNA sequence,
   wherein the nucleotide in the oligonucleotide that is opposite the target adenosine is not 2'-OMe modified.

\* \* \* \* \*

SEQUENCE LISTING

<160> NUMBER OF SEQ ID NOS: 47

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1
cgcgcgtttt cgcgcggcug aaccacugca c                                  31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 2
cgcgcgtttt cgcgcggaga uacucacaau u                                  31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 3
cgcgcgtttt cgcgcgcguu gaccuccacu c                                  31

<210> SEQ ID NO 4
<211> LENGTH: 4440
<212> TYPE: DNA
<213> ORGANISM: Homo sapiens

<400> SEQUENCE: 4
atgcagaggt cgcctctgga aaaggccagc gttgtctcca aactttttt cagctggacc    60 agaccaattt tgaggaaagg atacagacag cgcctggaat tgtcagacat ataccaaatc   120
ccttctgttg attctgctga caatctatct gaaaaattgg aaagagaatg ggatagagag   180
ctggcttcaa agaaaaatcc taaactcatt aatgcccttc ggcgatgttt tttctggaga   240
tttatgttct atggaatctt tttatattta ggggaagtca ccaaagcagt acagcctctc   300
ttactgggaa gaatcatagc ttcctatgac ccggataaca aggaggaacg ctctatcgcg   360
atttatctag gcataggctt atgccttctc tttattgtga ggacactgct cctacaccca   420 gccattttg gccttcatca cattggaatg cagatgagaa tagctatgtt tagtttgatt   480
tataagaaga ctttaaagct gtcaagccgt gttctagata aaataagtat tggacaactt   540
gttagtctcc tttccaacaa cctgaacaaa tttgatgaag acttgcatt ggcacatttc   600 gtgtggatcg ctccttttgca agtggcactc tcatgggc taatctggga gttgttacag   660
gcgtctgcct tctgtggact tggtttcctg atagtccttg ccctttttca ggctgggcta   720

-continued

```
gggagaatga tgatgaagta cagagatcag agagctggga agatcagtga aagacttgtg   780
attacctcag aaatgattga aaatatccaa tctgttaagg catactgctg ggaagaagca   840
atggaaaaaa tgattgaaaa cttaagacaa acagaactga aactgactcg gaaggcagcc   900
tatgtgagat acttcaatag ctcagccttc ttcttctcag ggttcttttgt ggtgtttta   960 tctgtgcttc cctatgcact aatcaaagga atcatcctcc ggaaaatatt caccaccatc  1020
tcattctgca ttgttctgcg catggcggtc actcggcaat ttccctgggc tgtacaaaca  1080
tggtatgact ctcttggagc aataaacaaa atacaggatt tcttacaaaa gcaagaatat  1140
aagacattgg aatataactt aacgactaca gaagtagtga tggagaatgt aacagccttc  1200
tgggaggagg gatttgggga attatttgag aaagcaaaac aaaacaataa caatagaaaa  1260
acttctaatg gtgatgacag cctcttcttc agtaatttct cacttcttgg tactcctgtc  1320
ctgaaagata ttaatttcaa gatagaaaga ggacagttgt tggcggttgc tggatccact  1380
ggagcaggca agacttcact tctaatgatg attatgggag aactggagcc ttcagagggt  1440
aaaattaagc acagtggaag aatttcattc tgttctcagt tttcctggat tatgcctggc  1500
accattaaag aaaatatcat cttttggtgtt tcctatgatg aatatagata cagaagcgtc  1560
atcaaagcat gccaactaga agaggacatc tccaagtttg cagagaaaga caatatagtt  1620
cttggagaag gtggaatcac actgagtgga gaycaacgag caagaatttc tttagcaaga  1680
gcagtataca aagatgctga tttgtattta ttagactctc cttttggata cctagatgtt  1740
ttaacagaaa aagaaatatt tgaaagctgt gtctgtaaac tgatggctaa caaaactagg  1800
attttggtca cttctaaaat ggaacattta agaaagctg acaaaatatt aattttgcat  1860
gaaggtagca gctatttta tgggacattt tcagaactcc aaaatctaca gccagacttt  1920
agctcaaaac tcatgggatg tgattctttc gaccaattta gtgcagaaag aagaaattca  1980
atcctaactg agaccttaca ccgtttctca ttagaaggag atgctcctgt ctcctggaca  2040
gaaacaaaaa aacaatcttt taaacagact ggagagtttg gggaaaaaag gaagaattct  2100
attctcaatc caatcaactc tatacgaaaa ttttccattg tgcaaaagac tcccttacaa  2160
atgaatggca tcgaagagga ttctgatgag cctttagaga aaggctgtc cttagtacca  2220 gattctgagc agggagaggc gatactgcct cgcatcagcg tgatcagcac tggccccacg  2280
cttcaggcac gaaggaggca gtctgtcctg aacctgatga cacactcagt taaccaaggt  2340
cagaacattc accgaaagac aacagcatcc acacgaaaag tgtcactggc ccctcaggca  2400
aacttgactg aactggatat atattcaaga aggttatctc aagaaactgg cttgaaaata  2460
agtgaagaaa ttaacgaaga agacttaaag gagtgctttt ttgatgatat ggagagcata  2520
ccagcagtga ctacatggaa cacatacctt cgatatatta ctgtccacaa gagcttaatt  2580
tttgtgctaa tttggtgctt agtaatttt ctggcagagg tggctgcttc tttggttgtg  2640
ctgtggctcc ttggaaacac tcctcttcaa gacaaaggga atagtactca tagtagaaat  2700
aacagctatg cagtgattat caccagcacc agttcgtatt atgtgtttta catttacgtg  2760
ggagtagccg acactttgct tgctatggga ttcttcagag gtctaccact ggtgcatact  2820
ctaatcacag tgtcgaaaat tttacaccac aaaaatgttac attctgttct tcaagcacct  2880
atgtcaaccc tcaacacgtt gaaagcaggt gggattctta atagattctc caaagatata  2940
gcaattttgg atgaccttct gcctcttacc atatttgact tcatccagtt gttattaatt  3000
gtgattggag ctatagcagt tgtcgcagtt ttacaaccct acatctttgt tgcaacagtg  3060
ccagtgatag tggctttat tatgttgaga gcatatttcc tccaaacctc acagcaactc  3120
```

```
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttattttttc tggaacattt    3900
agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
```

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Recruiting portion

<400> SEQUENCE: 5
cgcgcgtttt cgcgcg                                                      16

<210> SEQ ID NO 6
<211> LENGTH: 35
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Recruiting portion
<220> FEATURE:
<221> NAME/KEY: modified_base
<222> LOCATION: (4)..(4)
<223> OTHER INFORMATION: a, c, u, g, to form a base pair
<220> FEATURE:
<221> NAME/KEY: modified_base
<222> LOCATION: (32)..(32)
<223> OTHER INFORMATION: a, c, u, g, to form a base pair

```
<400> SEQUENCE: 6
auanuauaac aauaugcuaa auguuguuau anuau                              35

<210> SEQ ID NO 7
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Recruiting portion

<400> SEQUENCE: 7
uauaacaaua ugcuaaaugu uguuaua                                       27

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting portion
<220> FEATURE:
<221> NAME/KEY: modified_base
<222> LOCATION: (1)..(17)
<223> OTHER INFORMATION: a, c, u, g
<220> FEATURE:
<221> NAME/KEY: modified_base
<222> LOCATION: (19)..(21)
<223> OTHER INFORMATION: a, c, u, g

<400> SEQUENCE: 8
nnnnnnnnnn nnnnnnncnn n                                             21

<210> SEQ ID NO 9
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gaguggagau caacg                                                    15

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctaagtac agggacatct tgc                                           23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```
agactccact tgttctttta aggag                                              25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgactgctaa gtacagggac atcttg                                             26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggagatgtt ttcacactcc aggt                                               24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctggccccag ttgtaatttg tga                                                23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgttcccag gcttgttcaa tagt                                               24

<210> SEQ ID NO 16
<211> LENGTH: 44
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 16
guguuggcca uggaacauau aacaauaugc uaaauguugu uaua                         44

<210> SEQ ID NO 17
<211> LENGTH: 44
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 17
uauaacaaua ugcuaaaugu uguuauagug uuggccaugg aaca                         44

```
<210> SEQ ID NO 18
<211> LENGTH: 44
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 18
guguuggcca uggaacauau aacaauaugc uaaauguugu uaua                          44

<210> SEQ ID NO 19
<211> LENGTH: 52
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 19
guguuggcca uggaacaaua guauaacaau augcuaaaug uuguuauagu au                 52

<210> SEQ ID NO 20
<211> LENGTH: 58
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 20
ggaauaguau aacaauaugc uaaauguugu uauaguaucc cguguuggcc auggaaca           58

<210> SEQ ID NO 21
<211> LENGTH: 58
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 21
guguuggcca uggaacagga auaguauaac aauaugcuaa auguuguuau aguauccc           58

<210> SEQ ID NO 22
<211> LENGTH: 58
<212> TYPE: RNA
<213> ORGANISM: Artificial Sequence
<220> FEATURE:
<223> OTHER INFORMATION: Description of Artificial Sequence: Synthetic
      GFP oligonucleotide construct

<400> SEQUENCE: 22
ggaauaguau aacaauaugc uaaauguugu uauaguaucc cguguuggcc auggaaca           58

<210> SEQ ID NO 23
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Recruiting portion
<220> FEATURE:
<221> NAME/KEY: modified_base
<222> LOCATION: (7)..(7)
```

```
<223> OTHER INFORMATION: a, c, u, g, to form a base pair
<220> FEATURE:
<221> NAME/KEY: modified_base
<222> LOCATION: (35)..(35)
<223> OTHER INFORMATION: a, c, u, g, to form a base pair

<400> SEQUENCE: 23
ggaauanuau aacaauaugc uaaauguugu uauanuaucc c                    41

<210> SEQ ID NO 24
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Recruiting portion
<220> FEATURE:
<221> NAME/KEY: modified_base
<222> LOCATION: (9)..(9)
<223> OTHER INFORMATION: a, c, u, g, to form a base pair
<220> FEATURE:
<221> NAME/KEY: modified_base
<222> LOCATION: (37)..(37)
<223> OTHER INFORMATION: a, c, u, g, to form a base pair

<400> SEQUENCE: 24
guggaauanu auaacaauau gcuaaauguu guuauanuau cccac                45

<210> SEQ ID NO 25
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Recruiting portion
<220> FEATURE:
<221> NAME/KEY: modified_base
<222> LOCATION: (5)..(5)
<223> OTHER INFORMATION: a, c, u, g, to form a base pair
<220> FEATURE:
<221> NAME/KEY: modified_base
<222> LOCATION: (9)..(9)
<223> OTHER INFORMATION: a, c, u, g, to form a base pair
<220> FEATURE:
<221> NAME/KEY: modified_base
<222> LOCATION: (37)..(37)
<223> OTHER INFORMATION: a, c, u, g, to form a base pair
<220> FEATURE:
<221> NAME/KEY: modified_base
<222> LOCATION: (41)..(41)
<223> OTHER INFORMATION: a, c, u, g, to form a base pair

<400> SEQUENCE: 25
guggnauanu auaacaauau gcuaaauguu guuauanuau nccac                45

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctggcacc attaaagaaa                                            20

<210> SEQ ID NO 27
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcatctttgt atactgctct tgct                                          24

<210> SEQ ID NO 28
<211> LENGTH: 66
<212> TYPE: RNA
<213> ORGANISM: Artificial Sequence
<220> FEATURE:
<223> OTHER INFORMATION: Description of Artificial Sequence: Synthetic
      A1AT oligonucleotide

<400> SEQUENCE: 28
ggaauaguau aacaauaugc uaaauguugu uauaguaucc ccaguccuu ucucgucgau    60 ggucag                                                              66

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccatcgacga gaaag                                                    15

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
catcgacaag aaag                                                     14

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tccaggccgt gcataagg                                                 18

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccccagcag cttcag                                                   16
```

```
<210> SEQ ID NO 33
<211> LENGTH: 161
<212> TYPE: DNA
<213> ORGANISM: Homo sapiens

<400> SEQUENCE: 33
atacctccac tcagccatga ttatataccg agacctgaaa ccccacaatg tgctgctttt     60
cacactgtat cccaatgctg ccatcattgc aaagattgct gactacggca ttgctcagta    120
ctgctgtaga atggggataa aaacatcaga gggcacacca g                        161

<210> SEQ ID NO 34
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 34 gct gac tac agc att gct cag                                           21
Ala Asp Tyr Ser Ile Ala Gln
1               5

<210> SEQ ID NO 35
<211> LENGTH: 7
<212> TYPE: PRT
<213> ORGANISM: Homo sapiens

<400> SEQUENCE: 35

Ala Asp Tyr Ser Ile Ala Gln
1               5

<210> SEQ ID NO 36
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 36 gct gac tac ggc att gct cag                                           21
Ala Asp Tyr Gly Ile Ala Gln
1               5

<210> SEQ ID NO 37
<211> LENGTH: 7
<212> TYPE: PRT
<213> ORGANISM: Homo sapiens

<400> SEQUENCE: 37

Ala Asp Tyr Gly Ile Ala Gln
1               5

<210> SEQ ID NO 38
<211> LENGTH: 70
<212> TYPE: RNA
<213> ORGANISM: Artificial Sequence
<220> FEATURE:
<223> OTHER INFORMATION: Description of Artificial Sequence: Synthetic
      LRRK2 oligonucleotide construct

<400> SEQUENCE: 38
guggaauagu auaacaauau gcuaaauguu guuauaguau cccacacuga gcaaugccgu     60
agucagcaau                                                            70
```

<210> SEQ ID NO 39
<211> LENGTH: 75
<212> TYPE: RNA
<213> ORGANISM: Artificial Sequence
<220> FEATURE:
<223> OTHER INFORMATION: Description of Artificial Sequence: Synthetic
      LRRK2 oligonucleotide construct

<400> SEQUENCE: 39
guggauuagu auaacaauau gcuaaauguu guuauaguau cccacguacu gagcaaugcc    60
guagucagca aucuu                                                    75

<210> SEQ ID NO 40
<211> LENGTH: 66
<212> TYPE: RNA
<213> ORGANISM: Artificial Sequence
<220> FEATURE:
<223> OTHER INFORMATION: Description of Artificial Sequence: Synthetic
      LRRK2 oligonucleotide construct

<400> SEQUENCE: 40
ggaauaguau aacaauaugc uaaauguugu uauaguaucc cacugagcaa ugccguaguc    60
agcaau                                                              66

<210> SEQ ID NO 41
<211> LENGTH: 71
<212> TYPE: RNA
<213> ORGANISM: Artificial Sequence
<220> FEATURE:
<223> OTHER INFORMATION: Description of Artificial Sequence: Synthetic
      LRRK2 oligonucleotide construct

<400> SEQUENCE: 41
ggaauaguau aacaauaugc uaaauguugu uauaguaucc cguacugagc aaugccguag    60
ucagcaaucu u                                                        71

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtttgagata cctccactca gc                                            22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aggtgcacga aaccctggtg                                               20

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic

```
          oligonucleotide
<220> FEATURE:
<221> NAME/KEY: misc_feature
<222> LOCATION: (7)..(26)
<223> OTHER INFORMATION: This region may encompass 2-20 nucleotides
<220> FEATURE:
<221> NAME/KEY: modified_base
<222> LOCATION: (7)..(26)
<223> OTHER INFORMATION: a, c, t, g, or inosine

<400> SEQUENCE: 44
cgcgcgnnnn nnnnnnnnnn nnnnncgcg cg                                      32

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (7)..(11)
<223> OTHER INFORMATION: This region may encompass 3-5 nucleotides

<400> SEQUENCE: 45
cgcgcgtttt tcgcgcg                                                      17

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 46
cgcgcgtttt cgcgcg                                                       16

<210> SEQ ID NO 47
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: May or may not be present
<220> FEATURE:
<221> NAME/KEY: modified_base
<222> LOCATION: (4)..(4)
<223> OTHER INFORMATION: a, g, c, or u
<220> FEATURE:
<221> NAME/KEY: modified_base
<222> LOCATION: (32)..(32)
<223> OTHER INFORMATION: a, g, c, or u
<220> FEATURE:
<221> NAME/KEY: misc_feature
<222> LOCATION: (32)..(35)
<223> OTHER INFORMATION: May or may not be present
<220> FEATURE:
<223> OTHER INFORMATION: See specification as filed for detailed
      description of substitutions and preferred embodiments

<400> SEQUENCE: 47
auanuauaac aauaugcuaa auguuguuau anuau                                  35
```